(12) United States Patent
Ortega et al.

(10) Patent No.: US 8,437,848 B2
(45) Date of Patent: May 7, 2013

(54) APPARATUS FOR TREATING THE PHYSIOLOGICAL ELECTRIC CONDUCTION OF THE HEART

(75) Inventors: Daniel Felipe Ortega, Buenos Aires (AR); Alberto German Giniger, Buenos Aires (AR)

(73) Assignee: Cardiac Pacemakers, Inc., St. Paul, MN (US)

( * ) Notice: Subject to any disclaimer, the term of this patent is extended or adjusted under 35 U.S.C. 154(b) by 601 days.

(21) Appl. No.: 12/249,479

(22) Filed: Oct. 10, 2008

(65) Prior Publication Data
US 2009/0093859 A1 Apr. 9, 2009

Related U.S. Application Data

(63) Continuation of application No. 11/300,242, filed on Dec. 13, 2005, now Pat. No. 8,346,358.

(30) Foreign Application Priority Data

Dec. 20, 2004 (AR) .............................. 20040104782

(51) Int. Cl.
*A61N 1/368* (2006.01)
(52) U.S. Cl.
USPC ....... 607/9; 607/11; 607/15; 607/36; 607/122
(58) Field of Classification Search ................ 607/9, 11, 607/15, 36, 122
See application file for complete search history.

(56) References Cited

U.S. PATENT DOCUMENTS

| 3,614,955 A | 10/1971 | Mirowski |
| 3,804,098 A | 4/1974 | Friedman |
| 3,866,615 A | 2/1975 | Hewson |
| 3,911,928 A | 10/1975 | Lagergren |
| 3,942,536 A | 3/1976 | Mirowski et al. |

(Continued)

FOREIGN PATENT DOCUMENTS

| AU | 2005319498 | 7/2011 |
| DE | 2827595 A1 | 4/1979 |

(Continued)

OTHER PUBLICATIONS

Alboni. *Bundle Branch Blocks Anatomically Located In The His Bundle*. Italian Cardiology Journal, vol. 10, No. 12, 1980. English translation thereof, followed by Italian publication.

(Continued)

*Primary Examiner* — Joseph Dietrich
(74) *Attorney, Agent, or Firm* — Schwegman Lundberg & Woessner, P.A.

(57) ABSTRACT

A new pacemaker apparatus for treating the physiological electric conduction of the heart that includes a conduction abnormality in a ventricle. The pacemaker includes a pulse generator and a pacing electrode located in the heart, the pulse generator providing pacing signals to the pacing electrode. The pacemaker further includes a signal generation circuit that generates electrical signals from heart-related feedback signals that indicate that the pacing electrode is delivering the pacing signals in a region at or near the His bundle of the heart. The combination of the pulse generator and the signal generation circuit indicates that the pacing electrode is delivering the pacing signals in the region, at or near the His bundle of the heart, to electrically bypass the conduction abnormality of the heart in the ventricle.

27 Claims, 9 Drawing Sheets

U.S. PATENT DOCUMENTS

| | | |
|---|---|---|
| 3,949,757 A | 4/1976 | Sabel |
| 3,995,623 A | 12/1976 | Blake et al. |
| 4,026,303 A | 5/1977 | Babotai |
| 4,030,508 A | 6/1977 | Thalen |
| 4,057,067 A | 11/1977 | Lajos |
| 4,106,512 A | 8/1978 | Bisping |
| 4,136,703 A | 1/1979 | Wittkampf |
| 4,154,247 A | 5/1979 | O'Neill |
| 4,217,913 A | 8/1980 | Dutcher |
| 4,258,725 A | 3/1981 | O'Neill |
| 4,278,093 A | 7/1981 | Lafortune et al. |
| 4,282,885 A | 8/1981 | Bisping |
| 4,289,134 A | 9/1981 | Bernstein |
| 4,289,144 A | 9/1981 | Gilman |
| 4,311,153 A | 1/1982 | Smits |
| 4,332,259 A | 6/1982 | McCorkle, Jr. |
| 4,365,639 A | 12/1982 | Goldreyer |
| 4,393,883 A | 7/1983 | Smyth et al. |
| 4,402,329 A | 9/1983 | Williams |
| 4,437,474 A | 3/1984 | Peers-Trevarton |
| 4,458,677 A | 7/1984 | McCorkle, Jr. |
| 4,458,695 A | 7/1984 | Peers-Trevarton |
| 4,463,765 A | 8/1984 | Gold |
| 4,469,104 A | 9/1984 | Peers-Trevarton |
| 4,497,326 A | 2/1985 | Curry |
| 4,540,236 A | 9/1985 | Peers-Trevarton |
| 4,543,956 A | 10/1985 | Herscovici |
| 4,549,548 A | 10/1985 | Wittkampf et al. |
| 4,559,951 A | 12/1985 | Dahl et al. |
| 4,567,901 A | 2/1986 | Harris |
| 4,570,642 A | 2/1986 | Kane et al. |
| 4,577,643 A | 3/1986 | Beranek |
| 4,589,420 A | 5/1986 | Adams et al. |
| 4,602,645 A | 7/1986 | Barrington et al. |
| 4,603,705 A | 8/1986 | Speicher et al. |
| 4,624,265 A | 11/1986 | Grassi |
| 4,624,266 A | 11/1986 | Kane |
| 4,627,439 A | 12/1986 | Harris |
| 4,630,204 A | 12/1986 | Mortara |
| 4,633,880 A | 1/1987 | Osypka et al. |
| 4,641,649 A | 2/1987 | Walinsky et al. |
| 4,643,201 A | 2/1987 | Stokes |
| 4,646,755 A | 3/1987 | Kane |
| 4,649,937 A | 3/1987 | DeHaan et al. |
| 4,649,938 A | 3/1987 | McArthur |
| 4,664,113 A | 5/1987 | Frisbie et al. |
| 4,667,686 A | 5/1987 | Peers-Travarton |
| H356 H | 11/1987 | Stokes et al. |
| 4,721,115 A | 1/1988 | Owens |
| 4,751,931 A | 6/1988 | Briller et al. |
| 4,784,161 A | 11/1988 | Skalsky et al. |
| 4,785,815 A | 11/1988 | Cohen |
| 4,799,486 A | 1/1989 | DuFault |
| 4,799,493 A | 1/1989 | DuFault |
| 4,819,647 A | 4/1989 | Byers et al. |
| 4,819,661 A | 4/1989 | Heil, Jr. et al. |
| 4,819,662 A | 4/1989 | Heil, Jr. et al. |
| 4,876,109 A | 10/1989 | Mayer et al. |
| 4,886,074 A | 12/1989 | Bisping |
| 4,892,102 A | 1/1990 | Astrinsky |
| 4,895,152 A | 1/1990 | Callaghan et al. |
| 4,922,607 A | 5/1990 | Doan et al. |
| 4,922,927 A | 5/1990 | Fine et al. |
| 4,924,881 A | 5/1990 | Brewer |
| 4,953,564 A | 9/1990 | Berthelsen |
| 4,967,766 A | 11/1990 | Bradshaw |
| 4,972,848 A | 11/1990 | DiDomenico et al. |
| 4,994,078 A | 2/1991 | Jarvik |
| 5,002,067 A | 3/1991 | Berthelsen et al. |
| 5,007,864 A | 4/1991 | Stutz, Jr. |
| 5,016,646 A | 5/1991 | Gotthardt et al. |
| 5,050,001 A | 9/1991 | Kupersmith et al. |
| 5,056,516 A | 10/1991 | Spehr |
| 5,063,932 A | 11/1991 | Dahl et al. |
| 5,076,285 A | 12/1991 | Hess et al. |
| 5,083,564 A | 1/1992 | Scherlag |
| 5,092,879 A | 3/1992 | Jarvik |
| 5,129,404 A | 7/1992 | Spehr et al. |
| 5,144,960 A | 9/1992 | Mehra et al. |
| 5,152,299 A | 10/1992 | Soukup |
| 5,174,289 A | 12/1992 | Cohen |
| 5,179,962 A | 1/1993 | Dutcher et al. |
| 5,181,511 A | 1/1993 | Nickolls et al. |
| 5,223,226 A | 6/1993 | Wittmar et al. |
| 5,242,430 A | 9/1993 | Arenas et al. |
| 5,255,693 A | 10/1993 | Dutcher et al. |
| 5,259,394 A | 11/1993 | Bens |
| 5,259,395 A | 11/1993 | Li |
| 5,267,560 A | 12/1993 | Cohen |
| 5,275,620 A | 1/1994 | Darby et al. |
| 5,282,845 A | 2/1994 | Bush et al. |
| 5,299,569 A | 4/1994 | Wernicke et al. |
| 5,300,108 A | 4/1994 | Rebell et al. |
| 5,304,219 A | 4/1994 | Chernoff et al. |
| 5,306,292 A | 4/1994 | Lindegren |
| 5,313,953 A | 5/1994 | Yomtov et al. |
| 5,320,642 A | 6/1994 | Scherlag |
| 5,324,327 A | 6/1994 | Cohen |
| 5,336,252 A | 8/1994 | Cohen |
| 5,342,414 A | 8/1994 | Mehra |
| 5,344,439 A | 9/1994 | Otten |
| 5,358,516 A | 10/1994 | Myers et al. |
| 5,366,496 A | 11/1994 | Dahl et al. |
| 5,370,665 A | 12/1994 | Hudrlik |
| 5,374,286 A | 12/1994 | Morris |
| 5,381,790 A | 1/1995 | Kanesaka |
| 5,393,929 A | 2/1995 | Yagihashi |
| 5,405,373 A | 4/1995 | Petersson et al. |
| 5,411,544 A | 5/1995 | Mar et al. |
| 5,425,755 A | 6/1995 | Doan |
| 5,433,735 A | 7/1995 | Zanakis et al. |
| 5,439,391 A | 8/1995 | McEtchin et al. |
| 5,447,533 A | 9/1995 | Vachon et al. |
| 5,447,534 A | 9/1995 | Jammet |
| 5,456,706 A | 10/1995 | Pless et al. |
| 5,456,708 A | 10/1995 | Doan et al. |
| 5,466,253 A | 11/1995 | Doan |
| 5,476,497 A | 12/1995 | Mower et al. |
| 5,476,499 A | 12/1995 | Hirschberg |
| 5,476,501 A | 12/1995 | Stewart et al. |
| 5,476,502 A | 12/1995 | Rubin |
| 5,492,119 A | 2/1996 | Abrams |
| 5,500,008 A | 3/1996 | Fain |
| 5,514,172 A | 5/1996 | Mueller |
| 5,515,848 A | 5/1996 | Corbett, III et al. |
| 5,522,874 A | 6/1996 | Gates |
| 5,524,338 A | 6/1996 | Martynuik et al. |
| 5,527,344 A | 6/1996 | Arzbaecher et al. |
| 5,531,780 A | 7/1996 | Vachon |
| 5,545,201 A | 8/1996 | Helland et al. |
| 5,554,178 A | 9/1996 | Dahl et al. |
| 5,571,163 A | 11/1996 | Helland |
| 5,578,068 A | 11/1996 | Laske et al. |
| 5,593,405 A | 1/1997 | Osypka |
| 5,593,433 A | 1/1997 | Spehr et al. |
| 5,609,158 A | 3/1997 | Chan |
| 5,628,778 A | 5/1997 | Kruse et al. |
| 5,628,779 A | 5/1997 | Bornzin et al. |
| 5,634,829 A | 6/1997 | Kerul |
| 5,634,899 A | 6/1997 | Shapland et al. |
| 5,674,272 A | 10/1997 | Bush et al. |
| 5,674,274 A | 10/1997 | Morgan et al. |
| 5,683,447 A | 11/1997 | Bush et al. |
| 5,702,427 A | 12/1997 | Ecker et al. |
| 5,709,753 A | 1/1998 | Olson et al. |
| 5,716,390 A | 2/1998 | Li |
| 5,718,720 A | 2/1998 | Prutchi et al. |
| 5,720,099 A | 2/1998 | Parker et al. |
| 5,728,140 A | 3/1998 | Salo et al. |
| 5,733,323 A | 3/1998 | Buck et al. |
| 5,755,766 A | 5/1998 | Chastain et al. |
| 5,769,881 A | 6/1998 | Schroeppel et al. |
| 5,772,693 A | 6/1998 | Brownlee |
| 5,782,898 A | 7/1998 | Dahl et al. |
| 5,800,464 A | 9/1998 | Kieval |
| 5,800,465 A | 9/1998 | Thompson et al. |
| 5,807,306 A | 9/1998 | Shapland et al. |

| | | |
|---|---|---|
| 5,810,887 A | 9/1998 | Accorti, Jr. et al. |
| 5,814,077 A | 9/1998 | Sholder et al. |
| 5,814,079 A | 9/1998 | Kieval |
| 5,832,062 A | 11/1998 | Drake |
| 5,851,227 A | 12/1998 | Spehr |
| 5,861,013 A | 1/1999 | Peck et al. |
| 5,871,506 A | 2/1999 | Mower |
| 5,871,529 A | 2/1999 | Bartig et al. |
| 5,871,531 A | 2/1999 | Struble |
| 5,876,399 A | 3/1999 | Chia et al. |
| 5,876,431 A | 3/1999 | Spehr et al. |
| 5,916,214 A | 6/1999 | Cosio et al. |
| 5,925,045 A | 7/1999 | Reimels et al. |
| 5,935,159 A | 8/1999 | Cross, Jr. et al. |
| 5,941,868 A | 8/1999 | Kaplan |
| 5,944,710 A | 8/1999 | Dev et al. |
| 5,964,795 A | 10/1999 | McVenes et al. |
| 5,972,416 A | 10/1999 | Reimels et al. |
| 5,995,871 A | 11/1999 | Knisley |
| 6,006,139 A | 12/1999 | Kruse et al. |
| 6,007,476 A | 12/1999 | Wascher et al. |
| 6,024,739 A | 2/2000 | Ponzi et al. |
| 6,059,726 A | 5/2000 | Lee et al. |
| 6,070,104 A | 5/2000 | Hine et al. |
| 6,086,582 A | 7/2000 | Altman et al. |
| 6,096,069 A | 8/2000 | Bischoff |
| 6,123,084 A | 9/2000 | Jandak et al. |
| 6,141,588 A | 10/2000 | Cox et al. |
| 6,141,594 A | 10/2000 | Flynn et al. |
| 6,161,029 A | 12/2000 | Spreigl et al. |
| 6,165,164 A | 12/2000 | Hill et al. |
| 6,212,434 B1 | 4/2001 | Scheiner et al. |
| 6,219,581 B1 | 4/2001 | Schaldach et al. |
| 6,230,061 B1 | 5/2001 | Hartung |
| 6,236,887 B1 | 5/2001 | Ben-Haim et al. |
| 6,254,573 B1 | 7/2001 | Haim et al. |
| 6,256,541 B1 | 7/2001 | Heil et al. |
| 6,267,778 B1 | 7/2001 | Cohen |
| 6,309,370 B1 | 10/2001 | Haim et al. |
| 6,341,235 B1 | 1/2002 | Mower |
| 6,345,204 B1 | 2/2002 | Scheiner et al. |
| 6,351,679 B1 | 2/2002 | Ainslie |
| 6,358,247 B1 | 3/2002 | Altman et al. |
| 6,363,286 B1 | 3/2002 | Zhu et al. |
| 6,416,510 B1 | 7/2002 | Altman et al. |
| 6,463,334 B1 | 10/2002 | Flynn et al. |
| 6,468,263 B1 | 10/2002 | Fischell et al. |
| 6,471,697 B1 | 10/2002 | Lesh |
| 6,484,057 B2 | 11/2002 | Ideker et al. |
| 6,505,082 B1 | 1/2003 | Scheiner et al. |
| 6,535,766 B1 | 3/2003 | Thompson et al. |
| 6,540,725 B1 | 4/2003 | Ponzi |
| 6,542,775 B2 | 4/2003 | Ding et al. |
| 6,544,270 B1 | 4/2003 | Zhang |
| 6,547,787 B1 | 4/2003 | Altman et al. |
| 6,556,874 B2 | 4/2003 | Audoglio |
| 6,560,489 B2 | 5/2003 | Hauck |
| 6,575,931 B1 | 6/2003 | Ponzi |
| 6,585,716 B2 | 7/2003 | Altman |
| 6,606,517 B1 | 8/2003 | Park et al. |
| 6,609,027 B2 | 8/2003 | Kroll et al. |
| 6,623,473 B1 | 9/2003 | Ponzi |
| 6,623,474 B1 | 9/2003 | Ponzi |
| 6,643,546 B2 | 11/2003 | Mathis et al. |
| 6,650,940 B1 | 11/2003 | Zhu et al. |
| 6,702,744 B2 | 3/2004 | Mandrusov et al. |
| 6,702,777 B2 | 3/2004 | Haim et al. |
| 6,718,206 B2 | 4/2004 | Casavant |
| 6,766,190 B2 | 7/2004 | Ferek-Petric et al. |
| 6,768,923 B2 | 7/2004 | Ding et al. |
| 6,801,807 B2 | 10/2004 | Abrahamson |
| 6,804,555 B2 | 10/2004 | Warkentin |
| 6,810,286 B2 | 10/2004 | Donovan et al. |
| 6,855,124 B1 | 2/2005 | Gonzalez et al. |
| 6,901,289 B2 | 5/2005 | Dahl et al. |
| 6,905,476 B2 | 6/2005 | Ponzi |
| 6,907,285 B2 | 6/2005 | Denker et al. |
| 6,909,920 B2 | 6/2005 | Lokhoff et al. |
| 6,915,169 B2 | 7/2005 | Flynn et al. |
| 6,931,286 B2 | 8/2005 | Sigg et al. |
| 6,937,897 B2 | 8/2005 | Min et al. |
| 7,027,876 B2 | 4/2006 | Casavant et al. |
| 7,039,168 B1 | 5/2006 | Potts |
| 7,039,462 B2 | 5/2006 | Pastore et al. |
| 7,062,544 B1 | 6/2006 | Ollis |
| 7,096,051 B1 | 8/2006 | Alder |
| 7,113,825 B2 | 9/2006 | Pastore et al. |
| 7,130,682 B2 | 10/2006 | Stahmann et al. |
| 7,187,970 B2 | 3/2007 | Shemer et al. |
| 7,245,973 B2 | 7/2007 | Liu et al. |
| 7,257,443 B2 | 8/2007 | Pastore et al. |
| 7,280,872 B1 | 10/2007 | Mosesov et al. |
| 7,317,950 B2 | 1/2008 | Lee |
| 7,319,900 B2 | 1/2008 | Kim et al. |
| 7,359,837 B2 | 4/2008 | Drew |
| 7,392,095 B2 | 6/2008 | Flynn et al. |
| 7,395,042 B2 | 7/2008 | Alder |
| 7,400,931 B2 | 7/2008 | Mandrusov et al. |
| 7,460,914 B2 | 12/2008 | Mandrusov et al. |
| 7,509,170 B2 | 3/2009 | Zhang et al. |
| 7,512,440 B2 | 3/2009 | Ortega et al. |
| 7,529,584 B2 | 5/2009 | Laske et al. |
| 7,792,580 B2 | 9/2010 | Borowitz et al. |
| 7,817,784 B2 | 10/2010 | Wang et al. |
| 8,005,544 B2 | 8/2011 | Zhu et al. |
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 8,078,287 B2 | 12/2011 | Liu et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0049478 A1 | 4/2002 | Ding et al. |
| 2002/0058981 A1 | 5/2002 | Zhu et al. |
| 2002/0099413 A1 | 7/2002 | Mower |
| 2002/0120318 A1* | 8/2002 | Kroll et al. ............ 607/149 |
| 2002/0169484 A1 | 11/2002 | Mathis et al. |
| 2002/0183720 A1 | 12/2002 | Hill et al. |
| 2002/0193836 A1 | 12/2002 | Schmidt |
| 2002/0198583 A1 | 12/2002 | Rock et al. |
| 2003/0009145 A1 | 1/2003 | Struijker-Boudier |
| 2003/0032938 A1 | 2/2003 | Altman |
| 2003/0069625 A1 | 4/2003 | Ley et al. |
| 2003/0078625 A1 | 4/2003 | Casavant |
| 2003/0093104 A1 | 5/2003 | Bonner et al. |
| 2003/0105492 A1 | 6/2003 | Ding et al. |
| 2003/0105496 A1 | 6/2003 | Yu et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |
| 2003/0163184 A1 | 8/2003 | Scheiner et al. |
| 2003/0171723 A1 | 9/2003 | Ponzi |
| 2003/0195470 A1 | 10/2003 | Ponzi |
| 2004/0006265 A1 | 1/2004 | Alhussiny |
| 2004/0064176 A1* | 4/2004 | Min et al. ............ 607/126 |
| 2004/0104782 A1 | 6/2004 | Ruffieux |
| 2004/0106958 A1 | 6/2004 | Mathis et al. |
| 2004/0122484 A1 | 6/2004 | Hatlestad et al. |
| 2004/0153127 A1 | 8/2004 | Gordon et al. |
| 2004/0186546 A1 | 9/2004 | Mandrusov et al. |
| 2004/0213770 A1 | 10/2004 | Seward et al. |
| 2004/0214182 A1 | 10/2004 | Sharma et al. |
| 2004/0215240 A1 | 10/2004 | Lovett et al. |
| 2004/0215249 A1 | 10/2004 | Corbucci |
| 2004/0215251 A1 | 10/2004 | Sharma et al. |
| 2004/0247093 A1 | 12/2004 | Potts et al. |
| 2004/0260374 A1 | 12/2004 | Zhang et al. |
| 2005/0049516 A1 | 3/2005 | Ideker |
| 2005/0075677 A1 | 4/2005 | Ganion et al. |
| 2005/0125041 A1 | 6/2005 | Min et al. |
| 2005/0136385 A1 | 6/2005 | Mann |
| 2005/0137671 A1 | 6/2005 | Liu et al. |
| 2005/0152516 A1 | 7/2005 | Wang et al. |

| | | | |
|---|---|---|---|
| 2005/0159725 A1 | 7/2005 | Tockman et al. | |
| 2005/0203580 A1 | 9/2005 | Prentice et al. | |
| 2005/0267557 A1 | 12/2005 | Flynn et al. | |
| 2005/0277993 A1 | 12/2005 | Mower | |
| 2006/0030810 A1 | 2/2006 | Mandrusov et al. | |
| 2006/0064027 A1 | 3/2006 | Borowitz et al. | |
| 2006/0095860 A1 | 5/2006 | Wada et al. | |
| 2006/0104596 A1 | 5/2006 | Askins et al. | |
| 2006/0116596 A1 | 6/2006 | Zhou et al. | |
| 2006/0136001 A1 | 6/2006 | Ortega et al. | |
| 2006/0142812 A1 | 6/2006 | Ortega et al. | |
| 2006/0224197 A1 | 10/2006 | Havel et al. | |
| 2006/0224224 A1 | 10/2006 | Muhlenberg et al. | |
| 2007/0027488 A1 | 2/2007 | Kaiser et al. | |
| 2007/0060961 A1 | 3/2007 | Echt et al. | |
| 2007/0093872 A1 | 4/2007 | Chirife et al. | |
| 2007/0093874 A1 | 4/2007 | Chirife et al. | |
| 2007/0129764 A1 | 6/2007 | Burnes | |
| 2007/0232949 A1 | 10/2007 | Saksena | |
| 2007/0233216 A1 | 10/2007 | Liu et al. | |
| 2007/0239219 A1 | 10/2007 | Salo et al. | |
| 2008/0262587 A1 | 10/2008 | Flynn et al. | |
| 2008/0319496 A1 | 12/2008 | Zhu et al. | |
| 2008/0319499 A1 | 12/2008 | Zhu et al. | |
| 2008/0319500 A1 | 12/2008 | Zhu et al. | |
| 2008/0319501 A1 | 12/2008 | Zhu et al. | |
| 2009/0005830 A1 | 1/2009 | Zhu et al. | |
| 2009/0005832 A1 | 1/2009 | Zhu et al. | |
| 2009/0005846 A1 | 1/2009 | Zhu et al. | |
| 2009/0054942 A1 | 2/2009 | Zhu et al. | |
| 2009/0093861 A1 | 4/2009 | Ortega et al. | |
| 2009/0099619 A1 | 4/2009 | Lessmeier et al. | |
| 2009/0105778 A1 | 4/2009 | Lee et al. | |
| 2009/0259272 A1 | 10/2009 | Reddy et al. | |
| 2010/0042176 A1 | 2/2010 | Snell | |
| 2010/0318147 A1 | 12/2010 | Forslund et al. | |
| 2011/0264158 A1 | 10/2011 | Dong et al. | |
| 2011/0264168 A1 | 10/2011 | Dadd et al. | |
| 2011/0307026 A1 | 12/2011 | Zhu et al. | |
| 2011/0319772 A1 | 12/2011 | Ingle | |
| 2011/0319956 A1 | 12/2011 | Zhu et al. | |
| 2012/0041500 A1 | 2/2012 | Zhu et al. | |
| 2012/0041503 A1 | 2/2012 | Zhu et al. | |
| 2012/0053651 A1 | 3/2012 | Zhu et al. | |
| 2012/0101539 A1 | 4/2012 | Zhu et al. | |
| 2012/0239106 A1 | 9/2012 | Maskara et al. | |

FOREIGN PATENT DOCUMENTS

| | | |
|---|---|---|
| DE | 3712082 A1 | 10/1988 |
| EP | 0042551 A1 | 12/1981 |
| EP | 0057877 A1 | 8/1982 |
| EP | 0282047 A2 | 9/1988 |
| EP | 0321764 A1 | 6/1989 |
| EP | 0452278 A2 | 10/1991 |
| EP | 0573275 A2 | 12/1993 |
| EP | 0591053 A1 | 4/1994 |
| EP | 0612538 A2 | 8/1994 |
| EP | 0620024 A1 | 10/1994 |
| EP | 0672431 A2 | 9/1995 |
| EP | 0709111 A2 | 5/1996 |
| EP | 1234597 A2 | 8/2002 |
| FR | 2465489 A1 | 3/1981 |
| FR | 2575925 A1 | 7/1986 |
| FR | 2757773 A1 | 7/1998 |
| GB | 2240721 | 8/1991 |
| JP | 10052507 A1 | 2/1998 |
| WO | WO-92/20401 A1 | 11/1992 |
| WO | WO-94/22525 A1 | 10/1994 |
| WO | WO-96/15665 A2 | 5/1996 |
| WO | WO-97/40883 A1 | 11/1997 |
| WO | WO-00/74773 A1 | 12/2000 |
| WO | WO-03/035170 A1 | 5/2003 |
| WO | WO-2005/011475 A2 | 2/2005 |
| WO | WO-2006/068880 A1 | 6/2006 |
| WO | WO-2008/063498 A1 | 5/2008 |
| WO | WO-2009/006321 A2 | 1/2009 |
| WO | WO-2009/006325 A1 | 1/2009 |
| WO | WO-2009/006327 A1 | 1/2009 |
| WO | WO-2009/006331 A1 | 1/2009 |
| WO | WO-2009/006339 A1 | 1/2009 |
| WO | WO-2009/078751 A1 | 6/2009 |
| WO | WO-2010/042910 A1 | 4/2010 |
| WO | WO-2010/071849 A2 | 6/2010 |
| WO | WO-2011/139691 A1 | 11/2011 |
| WO | WO-2012/005985 A2 | 1/2012 |
| WO | WO-2012125273 A2 | 9/2012 |

OTHER PUBLICATIONS

Brochure-Product. *ATROSTIM Phrenic Nerve Stimulator*. AtroTech Oy, P.O. Box 28, FIN-33721 Tampere, Finland, 2 pgs. (Jun. 2004).

Furman et al. *A Practice of Cardiac Pacing*. Permanent Pacemaker Implementation, Chapter 5, pp. 97-127. Futura Publishing Co., Inc., Mount Kisco, NY (1986).

Lupi et al. *Effects of Right Ventricular Pacing on Intra-Left Ventricular Electromechanical Activation in Patients With Native Narrow QRS*. American Journal of Cardiology, 2006;98:219-222.

1997, Narula, M.D. *Longitudinal Dissociation In The His Bundle. Bundle Branch Block Due To Asynchronous Conduction Within The His Bundle In Man*. Circulation, vol. 56, No. 6, Dec. 1977.

Puech et al. *Narrowing and normalization of QRS by stimulation of the His bundle in complete left bundle branch block*. Scholarly Journal of the French Cardiology Society, vol. 72, No. 8, Aug. 1979. English translation thereof, followed by French publication.

Ravazzi et al. *Improvement of Interventricular Activation Time Using Biphasic Pacing Pulses at Different Sites on Right Ventricle Sepal Wall*. Progress in Biomedical Research, pp. 248-253 (Jun. 1999).

Saksena et al. *Electrical Therapy for Cardiac Arrhythmias*. Pacemaker Implantation Techniques, Chapter 9, pp. 173, 181-183, W.B. Saunders Co., Philadelphia, PA (1990).

Sweeney et al. *Adverse Effect of Ventricular Pacing on Heart Failure and Atrial Fibrillation Among Patients With Normal Baseline QRS Duration in a Clinical Trial of Pacemaker Therapy for Sinus Node Dysfunction*. Circulation, 2003;107:2932-2937.

Sweeney et al. *Heart Failure During Cardiac Pacing*. Circulation, 2006;113:2082-2088.

Tanabe et al. *Biventricular Pacing Worsened Dyssynchrony In Heart Failure Patient With Right-Bundle Branch Block*. Int'l Journal of Cardiology, in press 2008 (doi:10.1016/j.ijcard.2008.06.063).

"U.S. Appl. No. 10/861,078, Non Final Office Action mailed Oct. 6, 2006", 10 pgs.

"U.S. Appl. No. 10/861,078, Notice of Allowance mailed Feb. 7, 2007", 9 pgs.

"U.S. Appl. No. 10/861,078, Response filed Nov. 17, 2006 to Non Final Office Action mailed Oct. 6, 2006", 5 pgs.

"U.S. Appl. No. 11/300,242, Non Final Office Action mailed May 12, 2011", 9 pgs.

"U.S. Appl. No. 12/147,293, Notice of Allowance mailed Apr. 8, 2011", 12 pgs.

"U.S. Appl. No. 12/147,317, Examiner Interview Summary mailed Mar. 15, 2011", 3 pgs.

"U.S. Appl. No. 12/147,317, Response filed Jun. 27, 2011 to Non Final Office Action mailed Dec. 28, 2010", 11 pgs.

"U.S. Appl. No. 12/147,339, Notice of Allowance mailed Mar. 30, 2011", 9 pgs.

"U.S. Appl. No. 12/147,356, Notice of Allowance mailed Jun. 30, 2011", 15 pgs.

"U.S. Appl. No. 12/147,369, Notice of Allowance mailed Apr. 21, 2011", 7 pgs.

"U.S. Appl. No. 12/147,376, Final Office Action mailed Apr. 20, 2011", 11 pgs.

"U.S. Appl. No. 12/147,376, Response filed Aug. 22, 2011 to Final Office Action mailed Apr. 20, 2011", 8 pgs.

"U.S. Appl. No. 12/147,425, Notice of Allowance mailed Apr. 19, 2011", 8 pgs.

"U.S. Appl. No. 12/249,454, Non Final Office Action mailed Apr. 6, 2011", 8 pgs.

"U.S. Appl. No. 12/249,508, Restriction Requirement mailed Jun. 30, 2011", 6 pgs.

"U.S. Appl. No. 12/412,608, Non Final Office Action mailed May 26, 2011", 8 pgs.

"European Application Serial No. 05849548.2, Response filed Jun. 29, 2011 to Non Final Office Action mailed Dec. 20, 2010", 9.

"European Application Serial No. 08772198.1, Response filed Mar. 31, 2011 to Communication mailed Sep. 30, 2010", 11 pgs.

"European Application Serial No. 08781107.1, Response filed Jun. 14, 2011 to Communication mailed Dec. 14, 2010", 10 pgs.

"European Application Serial No. 08796045.6, Response filed Apr. 15, 2011 to Communication dated Oct. 8, 2010", 10 pgs.

"International Application Serial No. PCT/US2009/060293, International Preliminary Report on Patentability mailed Apr. 12, 2011", 10 pgs.

"Japanese Application Serial No. 2007-548289, Final Office Action dated Aug. 2, 2011", 3.

"Japanese Application Serial No. 2007-548289, Response filed May 20, 2011 to Office Action mailed Nov. 24, 2010", 9 pgs.

Chiu, Leo, et al., "Method for One-Click Deployment and or Configuration of Real-Time Software System Modifications", U.S. Appl. No. 60/558,921, filed Apr. 2, 2004, 8 pgs.

Wang, et al., "System for Managing Voice Files of a Voice Prompt Server", U.S. Appl. No. 10/835,444, (filed Apr. 28, 2004).

Wang, Sandy Chai-Jen, et al., "Improved Method and System for Managing Voic Prompt R Cordings Prior to Deploym NT", U.S. Appl. No. 60/532,271, filed Dec. 23, 2003, 12 pgs.

"U.S. Appl. No. 10/004,695, Amendment and Response filed Mar. 9, 2004 to Non-Final Office Action mailed Dec. 22, 2003", 8 pgs.

"U.S. Appl. No. 10/004,695, Non-Final Office Action mailed Dec. 22, 2003", 6 pgs.

"U.S. Appl. No. 10/004,695, Notice of Ailowance mailed Apr. 13, 2004", 7 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

"U.S. Appl. No. 10/745,302, Restriction Requirement mailed Aug. 12, 2005", 7 pgs.

"U.S. Appl. No. 11/300,242, Non-Final Office Action mailed Aug. 4, 2009", 9 pgs.

"U.S. Appl. No. 11/300,242, Non-Final Office Action mailed Mar. 27, 2008", 8 pgs.

"U.S. Appl. No. 11/300,242, Response filed Feb. 4, 2010 to Final Office Action mailed Aug. 4, 2009", 11 pgs.

"U.S. Appl. No. 11/300,242, Response filed Apr. 2, 2009 to Restriction Requirement mailed Dec. 15, 2008", 8 pgs.

"U.S. Appl. No. 11/300,242, Response filed Sep. 26, 2008 to Non-Final Office Action mailed Mar. 27, 2008", 10 pgs.

"U.S. Appl. No. 11/300,242, Restriction Requirement mailed Dec. 15, 2008", 10 pgs.

"U.S. Appl. No. 11/300,611, Amendment After Allowance Under 37 C.F.R. § 1.312 filed Feb. 9, 2009", 9 pgs.

"U.S. Appl. No. 11/300,611, Non-Final Office Action mailed Mar. 20, 2008", 7 pgs.

"U.S. Appl. No. 11/300,611, Notice of Allowance mailed Jan. 26, 2009", 7 pgs.

"U.S. Appl. No. 11/300,611, Response filed Sep. 22, 2008 to Non-Final Office Action mailed Mar. 20, 2008", 12 pgs.

"U.S. Appl. No. 11/300,611, Response to Rule 312 Communication mailed Feb. 26, 2009", 3 pgs.

"U.S. Appl. No. 12/147,293, Response filed Feb. 8, 2011 to Restriction Requirement mailed Oct. 8, 2010", 9 pgs.

"U.S. Appl. No. 12/147,293, Restriction Requirement mailed Oct. 8, 2010", 12 pgs.

"U.S. Appl. No. 12/147,317, Non-Final Office Action mailed Dec. 28, 2010", 7 pgs.

"U.S. Appl. No. 12/147,339, Notice of Allowance mailed Dec. 22, 2010", 8 pgs.

"U.S. Appl. No. 12/147,339, Response filed Oct. 20, 2010 to Restriction Requirement mailed Oct. 8, 2010", 7 pgs.

"U.S. Appl. No. 12/147,339, Restriction Requirement mailed Oct. 8, 2010", 7 pgs.

"U.S. Appl. No. 12/147,356 Restriction Requirement mailed Oct. 12, 2010", 7 pgs.

"U.S. Appl. No. 12/147,356, Notice of Allowance mailed Feb. 10, 2011", 17 pgs.

"U.S. Appl. No. 12/147,356, Response filed Nov. 10, 2010 to Restriction Requirement mailed Oct. 12, 2010", 9 pgs.

"U.S. Appl. No. 12/147,369, Non-Final Office Action mailed Sep. 10, 2010", 10 pgs.

"U.S. Appl. No. 12/147,369, Response filed Feb. 10, 2011 to Non Final Office Action mailed Sep. 10, 2010", 7 pgs.

"U.S. Appl. No. 12/147,376 Non-Final Office Action mailed Sep. 15, 2010", 9 pgs.

"U.S. Appl. No. 12/147,376, Response filed Feb. 15, 2011 to Non Final Office Action mailed Sep. 15, 2010", 9 pgs.

"U.S. Appl. No. 12/147,425 Non-Final Office Action mailed Sep. 15, 2010", 10 pgs.

"U.S. Appl. No. 12/147,425, Response filed Feb. 15, 2011 to Non Final Office Action mailed Sep. 15, 2010", 8 pgs.

"Australian Application Serial No. 2005319498, First Examiner Report mailed May 27, 2010", 3 pgs.

"Australian Application Serial No. 2005319498, Response filed Feb. 21, 2011 to First Examiner Report mailed May 27, 2010", 11 pgs.

"European Application Serial No. 05849548.2, Communication and Supplementary Partial European Search Report mailed Feb. 29, 2008", 8 pgs.

"European Application Serial No. 05849548.2, Communication mailed Jun. 9, 2009", 3 pgs.

"European Application Serial No. 05849548.2, Office Action mailed Dec. 20, 2010", 4 pgs.

"European Application Serial No. 05849548.2, Response filed Dec. 16, 2009 to Communication mailed Jun. 9, 2009", 10 pgs.

"European Application Serial No. 08772198.1, Office Action mailed Sep. 13, 2010", 6 pgs.

"European Application Serial No. 08781107.1, Invitation Pursuant to Rule 63(1) EPC mailed Jul. 13, 2010", 3 pgs.

"European Application Serial No. 08781107.1, Communication dated Feb. 9, 2010", 2 pgs.

"European Application Serial No. 08781107.1, Extended European Search Report mailed Nov. 25, 2010", 6 pgs.

"European Application Serial No. 08781107.1, Response filed Mar. 5, 2010 to Communication dated Feb. 9, 2010", 2 pgs.

"European Application Serial No. 08781107.1, Response filed Sep. 22, 2010 to the Invitation to Rule 63(1)", 11 pgs.

"European Application Serial No. 08796045.6, European Search Report mailed Sep. 21, 2010", 6 pgs.

"International Application Serial No. PCT/US05/45044, International Search Report mailed May 2, 2006", 1 pg.

"International Application Serial No. PCT/US05/45044, Written Opinion mailed May 2, 2006", 3 pgs.

"International Application Serial No. PCT/US08/68618, International Search Report mailed Nov. 26, 2008", 2 pgs.

"International Application Serial No. PCT/US08/68618, Written Opinion mailed Nov. 26, 2008", 6 pgs.

"International Application Serial No. PCT/US08/68627, International Search Report mailed Sep. 10, 2008", 1 pg.

"International Application Serial No. PCT/US08/68627, Written Opinion mailed Sep. 10, 2008", 4 pgs.

"International Application Serial No. PCT/US08/68630, International Search Report mailed Sep. 10, 2008", 1 pg.

"International Application Serial No. PCT/US08/68630, Written Opinion mailed Sep. 10, 2008", 4 pgs.

"International Application Serial No. PCT/US08/68632, International Search Report mailed Sep. 11, 2008", 2 pgs.

"International Application Serial No. PCT/US08/68632, Written Opinion mailed Sep. 11, 2008", 4 pgs.

"International Application Serial No. PCT/US08/68647, International Search Report mailed Sep. 22, 2008", 2 pgs.

"International Application Serial No. PCT/US08/68647, Written Opinion mailed Sep. 22, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2009/060293, Invitation to Pay Additional Fee mailed Dec. 18, 2009", 5 pgs.
"International Application Serial No. PCT/US2009/060293, International Search Report mailed Mar. 10, 2010", 6 pgs.
"International Application Serial No. PCT/US2009/060293, Written Opinion mailed Mar. 10, 2010", 10 pgs.
"Japanese Application Serial No. 2007-548289, Office Action mailed Nov. 24, 2010", (w/ English Translation), 7 pgs.
Barba-Pichardo, R., et al., "Permanent His-Bundle Pacing in Patients With Infra-Hisian Atrioventricular Block", *Rev Esp Cardiol. 59*(6), (Mar. 9, 2006), 553-558.
Bonanno, C., et al., "Effect on QRS Duration and Feasibility of Septal and Multisite Right Ventricular Pacing", *Cardiostimolazione*, 14(3), (Abstract Only), (Sep. 1996), p. 195.
Buckingham, T. A., et al., "Acute Hemodynamic Effects of Atrioventricular Pacing at Differing Sites in the Right Ventricle Individually and Simultaneously", *PACE*, 20[Pt. I], (Apr. 1997), 909-915.
Cantù, F., et al., "Validation of Criteria for Selective His Bundle and Para-Hisian Permanent Pacing", *PACE*, vol. 29, (Dec. 2006), 1326-1333.
Cantù, F., et al., "A Methodical Approach to Validate Selective His Bundle and para-Hisian Permanent Pacing", [Abstract] *Oasis*, (2006), 1 pg.
Catanzariti, D., et al., "Permanent His Bundle Pacing Does Not Induce Ventricular Dyssynchrony. An Echocardiographic Intrapatient Study of Comparison with Conventional Pacing", [Abstract] *Oasis*, (2006), 1 pg.
Chudzik, M., "Ventricular Endocardial Right Bifocal Stimulation in Treatment of Severe Dilated Cardiomyopathy Heart Failure in Patients with Unsuccessful Biventricular Pacemaker Implantation", [abstract CP07] *Europace Supplements*, vol. 7, (May 2005), 1 pg.
Deshmukh, P., et al., "Permanent, Direct His-Bundle Pacing: A Novel Approach to Cardiac Pacing in Patients With Normal His-Purkinje Activation", *Circulation*, 101(8), (Feb. 29, 2000), 869-877.
Deshmukh, P. M., et al., "Direct His-Bundle Pacing: Present and Future", *PACE*, vol. 27, Part II, (Jun. 2004), 862-870.
El-Sherif, N., et al., "Normalization of Bundle Branch Block Patterns by Distal His Bundle Pacing: Clinical and Experimental Evidence of Longitudinal Dissociation in the Pathologic His Bundle", *Circulation*, 57(3), (Mar. 1978), 473-483.
Golia, P., et al., "Multisite Pacing of Right Ventricle in Heart Failure: Echocardiographic Evaluation", [Abstract] *Cardiostimolazione*, vol. 14, No. 3, (Sep. 1996), 5 pgs.
Grosfeld, M. J.W., et al., "Testing a New Mechanism for Left Interventricular Septal Pacing: The Transseptal Route", *Europace*, vol. 4, (Oct. 2002), 439-444.
Hummel, J. D., et al., "Augmentation of Cardiac Output by Anodal Pacing", [Abstract] *Circulation*, 90(No. 4, Part 2), (Oct. 1994), p. I-69.
Kavanagh, K. M., et al., "Monophasic Versus Biphasic Cardiac Stimulation: Mechanism of Decreased Energy Requirements", *PACE*, vol. 13, No. 10, (Oct. 1990), 10 pgs.
Kutarski, A., et al., "Factors Influencing Differences of RVA & RVOT Pacing Hemodynamic Effects", [abstract CP05] *Europace Supplements*, vol. 7, (May 2005), p. 288.
Kutarski, A., et al., "Right Ventricular Outflow Tract and Dual Site Right Ventricular Pacing—The Comparison With Apex Pacing", [Abstract CP08] *Europace Supplements*, vol. 7, (May 2005), p. 288.
Lazarus, A., et al., "Reduction in Energy Pacing Thresholds by Overlapping Biphasic Stimulation Versus Conventional Bipolar Pacing", *PACE*, vol. 21, (Nov. 1998), 6 pgs.
Manolis, A. S., "The Deleterious Consequences of Right Ventricular Apical Pacing: Time to Seek Alternate Site Pacing", *PACE*, vol. 29, (Mar. 2006), 298-315.
Mond, H. G., et al., "The Right Ventricular Outflow Tract: The Road to Septal Pacing", *PACE*, vol. 30, (Apr. 2007), 482-491.
Moriña-Vazquez, P., et al., "Cardiac Resynchronization Through Selective His Bundle Pacing in a Patient with the So-Called InfraHis Atrioventricular Block", *PACE*, vol. 28, (Jul. 2005), 726-729.
Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", *Journal of the American College of Cardiology*, 47(10), (May 16, 2006), 1938-1945.
Padeletti, L., et al., "Physiologic Pacing: New Modalities and Pacing Sites", *PACE*, vol. 29, Supplement 2, (Dec. 2006), S73-S77.
Pastore, G., et al., "Different Degree of Ventricular Dyssyncrony Induced By Right Apical, Hissian and Para Hissian Ventricular Pacing", [Abstract] *Oasis*, (2006), 1 pg.
Pastore, G., et al., "Direct His-Bundle Pacing Preserves the Normal Left Activation Sequence: An Acute Echocardiographic Study", [Abstract] *Oasis*, (2006), 1 pg.
Reddy, G. S., "Bundle of His Stimulation System", U.S. Appl. No. 61/045,168, filed Apr. 15, 2008, 37 pgs.
Scheinman, M. M., et al., "Long-Term His-Bundle Pacing and Cardiac Function", *Circulation*, 101(8), (2000), 836-837.
Schoenfeld, M. H., "Alternative Site Pacing to Promote Cardiac Synchrony: Has Conventional Pacing Become Unconventional?", *Journal of the American College of Cardiology*, 47(10), (2006), 1946-1948.
Sotobata, I., et al., "Population distribution of Frank-vectorcardiographic measurements of healthy Japanese men", *Japanese Circulation Journal*, 39(8), (1975), 895-903.
Thakral, A, et al., "Effects of anodal vs. cathodal pacing on the mechanical performance of the isolated rabbit heart", *J. Appl Physiol.*, 89(3), (Sep. 2000), 1159-1164.
Tse, Hung-Fat, et al., "Selection of Permanent Ventricular Pacing Site: How Far Should We Go?", *Journal of the American College of Cardiology*, 48(8), (Sep. 26, 2006), 1649-1651.
Van Gelder, B. M., et al., "Hemodynamic Effect of RV Apex vs RV Septum Pacing in a Monoventricular and Biventricular Configuration in Patients with Heart Failure", [Abstract CP06] *Europace Supplements*, vol. 7, (May 2005), p. 288.
Victor, F., et al., "A Randomized Comparison of Permanent Septal Versus Apical Right Ventricular Pacing: Short-Term Results", *Journal of Cardiovascular Electrophysiology*, 17(3), (Mar. 2006), 238-242.
Winckels, S. K. G., et al., "High-Septal Pacing Reduces Ventricular Electrical Remodeling and Proarrhythmia in Chronic Atrioventricular Block Dogs", *Journal of the American College of Cardiology*, 50(9), (Aug. 28, 2007), 906-913.
Zanon, F., et al., "A Feasible Approach for Direct His-Bundle Pacing Using a New Steerable Catheter to Facilitate Precise Lead Placement", *Journal of Cardiovascular Electrophysiology*, 17(1), (Jan. 2006), 29-33.
Zanon, F., et al., "A New Technique for Direct His-Bundle Pacing: Acute and Mid-Term Electrical Data Results", [Abstract] *Oasis*, (2006), 1 pg.
Zanon, F., et al., "Direct His Bundle Pacing Preserves Coronary Perfusion Compared With Right Ventricular Apical Pacing: A Prospective, Cross-Over Mid-Term Study", *Europace*, vol. 10, (2008), 580-587.
Zhang, Y., et al., "His Electrogram Alternans Reveal Dual-Wavefront Inputs Into and Longitudinal Dissociation Within the Bundle of His", *Circulation*, 104(7), (2001), 832-838.
"U.S. Appl. No. 12/412,608, Notice of Allowance mailed Jun. 6, 2012", 7 pgs.
US 6,875,206, 4/2005, Ponzi (withdrawn).
"U.S. Appl. No. 11/300,242, Notice of Allowance mailed Jan. 24, 2012", 5 pgs.
"U.S. Appl. No. 11/300,242, Response filed Sep. 12, 2011 to Non Final Office Action mailed May 12, 2011", 8 pgs.
"U.S. Appl. No. 12/147,317, Final Office Action mailed Oct. 12, 2011", 6 pgs.

"U.S. Appl. No. 12/147,376, Response filed Feb. 29, 2012 to Non Final Office Action mailed Oct. 3, 2011", 6 pgs.
"U.S. Appl. No. 12/147,376, Non Final Office Action mailed Oct. 3, 2011", 8 pgs.
"U.S. Appl. No. 12/147,376, Notice of Allowance mailed Mar. 19, 2012", 7 pgs.
"U.S. Appl. No. 12/249,454, Examiner Interview Summary mailed Feb. 22, 2012", 3 pgs.
"U.S. Appl. No. 12/249,454, Final Office Action mailed Nov. 23, 2011", 8 pgs.
"U.S. Appl. No. 12/249,454, Response filed Apr. 2, 2012 to Final Office Action mailed Nov. 23, 2011", 12 pgs.
"U.S. Appl. No. 12/249,454, Response filed Aug. 30, 2011 to Non Final Office Action mailed Apr. 6, 2011", 14 pgs.
"U.S. Appl. No. 12/249,508, Notice of Allowance mailed Feb. 14, 2012", 7 pgs.
"U.S. Appl. No. 12/249,508, Notice of Allowance mailed Oct. 5, 2011", 9 pgs.
"U.S. Appl. No. 12/249,508, Response filed Aug. 30, 2011 to Restriction Requirement mailed Jun. 30, 2011", 8 pgs.
"U.S. Appl. No. 12/412,608, Final Office Action mailed Nov. 21, 2011", 6 pgs.
"U.S. Appl. No. 12/412,608, Response filed Sep. 26, 2011 to Non Final Office Action mailed May 26, 2011", 9 pgs.
"U.S. Appl. No. 60/947,308, filed Jun. 29, 2007", 47 pgs.
"U.S. Appl. No. 60/947,310, filed Jun. 29, 2007", 49 pgs.
"Coating Process for Composite Implants", *Medical Materials Update*, vol. 1, No. 12, (Jan. 1995), 3 pgs.
"European Application Serial No. 08796045.6, Office Action mailed Jan. 4, 2012", 4 pgs.
"Implant Attaches to Bone by Chemical Bond", *Medical Materials Update*, vol. 4, No. 7, (Aug. 1997), 2 pgs.
"International Application Serial No. PCT/US2009/068859, International Search Report mailed Jul. 5, 2010", 7 pgs.
"International Application Serial No. PCT/US2009/068859, Invitation to Pay Additional Fee mailed Apr. 15, 2010", 6 pgs.
"International Application Serial No. PCT/US2009/068859, Written Opinion mailed Jul. 5, 2010", 12 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.
"Japanese Application Serial No. 2007-548289, Response filed Oct. 26, 2011 to Office Action mailed Aug. 3, 2011", (w/ English Translation of Amended Claims), 10 pgs.
"Victrex's PEEK Used for Dialysis Machines", *Medical Material's Update*, vol. 3, No. 3, (Apr. 1996), pp. 1-2.
Al-Khadra, A., et al., "The Role of Electroporation in Defibrillation", *Circulation Research*, 87(9), (Oct. 2000), 797-804.
Avitall, B., et al., "Iontophoretic Transmyocardial Drug Delivery. A Novel Approach to Antiarrhythmic Drug Therapy", *Circulation*, 85(4), (1992), 1582-1593.
Barton, A. J., et al., "Bacterial Adhesion to Orthopedic Implant Polymers", *J. Biomed. Mat. Res.*, 30(3), (Mar. 1996), 403-410.
Dong, Y., et al., "His-Bundle Capture Verification and Monitoring", U.S. Appl. No. 61/328,248, filed Apr. 27, 2010, 40 pgs.
Flynn, D. M., et al., "Extendable and Retractable Lead Having a Snap-Fit Terminal Connector", U.S. Appl. No. 11/173,664, filed Jul. 1, 2005, 53 pgs.
Genc, S., et al., "Methodology for Locking Feature Selection in Integral Snap-Fit Assembly", *Proceedings of DETC '97, 1997 ASME Engineering Technical Conferences*, (Sep. 1997), 1-11.
Ha, S. W., et al., "Plasma-Sprayed Hydroxylapatite Coating on Carbon Fibre Reinforced Thermoplastic Composite Materials", *J. Mater. Sci. Mater. Med.*, vol. 5, No. 6-7. (1994), 481-484.
Ingle, Frank, et al., "Lead Motion Sensing Via Cable Microphonics", U.S. Appl. No. 61/359,430, filed Jun. 29, 2010, 52 pgs.
Jockisch, K. A., et al., "Biological Response to Chopped-Carbon-Fiber-Reinforced Peek", *J. Biomed. Mater. Res.*, 26(2), (1992), 133-146.
Kanno, S., et al., "Establishment of a simple and practical procedure applicable to therapeutic angiogenesis", *Circulation*, 99(20), (May 25, 1999), 2682-2687.
Kaye, D. M., et al., "Frequency-dependent activation of a constitutive nitric oxide synthase and regulation of contractile function in adult rat ventricular myocytes", *Circulation Research*, 78(2), (Feb. 1996), 217-24.
Knapp, C. P., et al., "Snap Fit Terminal Connector", U.S. Appl. No. 09/184,226, filed Nov. 2, 1998, 39 pgs.

Labhasetwar, V., et al., "Iontophoresis for Modulation of Cardiac Drug Delivery in Dogs", *Proc. Natl Acad Sci USA*, 92(7), (Mar. 28, 1995), 2612-2616.
Lin, T. W., et al., "Glass Peek Composite Promotes Proliferation and Osteocalcin of Human Osteoblastic Cells", *J. Biomed. Mater. Res.*, vol. 36, No. 2, (1997), 137-144.
MacNair, R., et al., "The Response of Primary Rat and Human Osteoblasts and an Immortalized Rat Osteoblast Cell Line to Orthopaedic Materials: Comparative Sensitivity of Several Toxicity Indices", *J. Mater. Sci. Mater. Med.*, vol. 8, No. 2, (1997), 105-111.
Mansourati, J., et al., "Left ventricular-based pacing in patients with chronic heart failure: comparison of acute hemodynamic benefits according to underlying heart disease", *Eur J Heart Fail.*, 2(2), (Jun. 2000), 195-199.
Meyer, M. R., et al., "Long-Term Durability of the Interface in FRP Composites After Exposure to Simulated Physiologic Saline Environments", *J. Biomed. Mater. Res.*, vol. 28, No. 10, (1994), 1221-1231.
Morrison, C., et al., "In Vitro Biocompatibility Testing of Polymers for Orthopaedic Implants Using Cultured Fibroblasts and Osteoblasts", *Biomaterials*, vol. 16, No. 13, (1995), pp. 987-992.
Qu, J, et al., "HCN2 overexpression in newborn and adult ventricular myocytes: distinct effects on gating and excitability", *Circ. Res.*, vol. 89(1), (Jul. 6, 2001), e8-14.
Qu, J, et al., "Sympathetic innervation alters activations of pacemaker current (If) in rat ventricle", *J. Physiol*, 526 Pt 3, (Aug. 1, 2000), 561-569.
Shi, W, et al., "Distribution and prevalence of hyperpolarization-activated cation channel (HCN) mRNA expression in cardiac tissues", *Circ. Res.*, vol. 85(1), (Jul. 9, 1999), e1-e6.
Soyer, J., et al., "Experimental Characterisation of a Carbon/PEEK Hip Porthesis in Fatigue", *Chirurgie*, 121, (1996), 658-663.
Takatsuki, et al., "Clinical Implications of "pure" Hisian pacing in addition to para-Hisian pacing for the diagnosis of supraventricular tachycardia", *Heart Rhythm 3*(12), (Dec. 8, 2006), 1412-1418.
Wenz, L. M., et al., "In Vitro Biocompatibiiity of Polyetheretherketone and Polysulfone Composites", *J. Biomed. Mater. Res.*, vol. 26, No. 2, (1990), 207-215
Yu, H., et al., "MinK-related peptide 1: A beta subunit for the HCN ion channel subunit family enhances expression and speeds activation", *Circ. Res.*, 88(12), (Jun. 22, 2001), e84-7.
Zhu, Q., et al., "Methods, Devices and Systems for Cardiac Pacing Therapies Using Intrinsic Activity", U.S. Appl. No. 61/139,117, filed Dec. 19, 2008, 22 pgs.
"U.S. Appl. No. 11/300,242, Notice of Allowance mailed May 8, 2012", 6 pgs.
"U.S. Appl. No. 11/300,242, Notice of Allowance mailed Aug. 24, 2012", 7 pgs.
"U.S. Appl. No. 12/147,317 , Response filed Apr. 11, 2012 to Final Office Action mailed Oct. 12, 2011", 8 pgs.
"U.S. Appl. No. 12/147,317, Notice of Allowance mailed Jul. 2, 2012", 7 pgs.
"U.S. Appl. No. 12/147,376, Notice of Allowance mailed Aug. 30, 2012", 7 pgs.
"U.S. Appl. No. 12/249,454, Non Final Office Action mailed Sep. 4, 2012", 8 pgs.
"U.S. Appl. No. 12/249,508, Notice of Allowance mailed Jun. 12, 2012", 7 pgs.
"U.S. Appl. No. 12/412,608, Notice of Allowance mailed Jun. 6, 2012", 7 pgs.
"U.S. Appl. No. 12/412,608, Response filed Apr. 18, 2012 to Final Office Action mailed Nov. 21, 2011", 7 pgs.
"European Application Serial No. 08796045.6, Response filed May 14, 2012 to Office Action mailed Jan. 4, 2012", 8 pgs.
"International Application Serial No. PCT/US2011/033944, International Preliminary Report on Patentability mailed Nov. 8, 2012", 9 pgs.
"International Application Serial No. PCT/US2012/026571, International Search Report mailed Oct. 18, 2012", 4 pgs.
"International Application Serial No. PCT/US2012/026571, Written Opinion mailed Oct. 18, 2012", 7 pgs.
"Japanese Application Serial No. 2007-548289, Office Action mailed Mar. 6, 2012", (w/ English Translation), 3 pgs.
"Japanese Application Serial No. 2007-548289, Office Action mailed Nov. 6, 2012", With English Translation, 3 pgs.
"Japanese Application Serial No. 2007-548289, Response filed Jun. 4, 2012 to Office Action mailed Mar. 6, 2012", 3 pgs.
Arcot-Krishnamurthy, S., et al., "Timing for His-Bundle Pacing", U.S. Appl. No. 13/277,617, filed Oct. 20, 2011, 40 pgs.

* cited by examiner

APPARATUS FOR TREATING THE PHYSIOLOGICAL ELECTRIC CONDUCTION OF THE HEART

RELATED PATENT DOCUMENTS

This patent document is a continuation under 35 U.S.C. §120 of U.S. patent application Ser. No. 11/300,242 filed on Dec. 13, 2005 now U.S. Pat. No. 8,346,358, published as U.S. 2006/0142812 on Jun. 29, 2006, which claims foreign priority to Argentina Patent Application No. 20040104782 filed on Dec. 20, 2004 by inventors Daniel Felipe Ortega and Alberto German Giniger and entitled "A NEW PACEMAKER WHICH REESTABLISHES OR KEEPS THE PHYSIOLOGICAL ELECTRIC CONDUCTION OF THE HEART AND A METHOD OF APPLICATION."

I. BACKGROUND OF THE INVENTION

The present invention relates to a new pacemaker which reestablishes or keeps the physiological electric synchrony of the heart and a method of application in the right ventricular septum, being possible to use, in order to facilitate the implantation and to avoid the connection and disconnection, a sheath to check a proper place and then screw the catheter in said place.

This method together with the pacemaker are responsible for the reestablishment and preservation of the physiological electric synchrony of the heart and is herein referred to as "EB (Electric Bypass)" due to the obtention of an alternative electric circuit and to the creation of the virtual electrode.

With the pacemaker of my invention and its method of application, a septal ventricular stimulation system with a high performance electrical and contractile synchrony is produced, thus significantly changing the implantation of a definitive pacemaker, making them more physiological. In the examples where my invention was applied, several patients with QRS narrowing were tested as well as those suffering disorders in the AV atrio-ventricular and intraventricular impulse conduction. The results show the QRS narrowing phenomena and the orientation of the depolarization with similar vectors compared to those of a depolarization by the His-Purkinje system.

A pacemaker is an electronic apparatus that produces electric impulses, intended to stimulate the cardiac muscle. The number of impulses produced per minute is called frequency. The mechanism is fed from electric power from batteries. These electric impulses are conducted to the heart by means of a cable (or electrode), so that the pacemaker itself (or pulse generator) is placed at a quite shallow surface underneath the skin, while the electrode is placed much more deeply inside the organism, up to the heart.

The first pacemakers, asynchronous, were only blind instruments that continuously produced 70 electric impulses per minute, carrying them up to the heart by means of an electrode. The electronic circuit consisted of a few diodes, transistors, resistors and a capacitor. One or more batteries provided the necessary power to feed the circuit and stimulate the heart. These pacemakers complied very well with their role when the patient's own rhythm was absolutely absent. However when the failure in the rhythm was just intermittent, the pacemaker slightly interfered with the normal rhythm, at the moments when it was reestablished.

Afterwards, the more intelligent pacemakers came out, Pacemakers on demand, that stopped functioning when the cardiac rhythm was reestablished. This supposed the introduction of new circuits, capable of detecting the electronic activity of the heart and new pacemakers were called "on demand" since they just started working when they were necessary.

Pacemakers on demand may be implanted in the atrium, in order to treat failures in the sinus node; or in the ventricle so as to treat the heart block.

An important advancement in the development of programmable pacemakers was to make them more versatile. The first ones only worked under a frequency set in factory, with fixed pulse energy and were able to detect certain level of cardiac electric activity also fixed.

It may be interesting to be able to change the stimulation frequency at certain moments, adjusting it to the organic needs. In other cases, a decrease in the pulse energy may be advantageous to save power and extend the duration of the pacemaker, or on the contrary, increase it if the muscle became resistant. In some patients, it would be useful to get the pacemaker to have higher o lower capacity for detecting electric impulses, in order to eliminate the influence of abnormal rhythms, or external interferences. All of the above-mentioned options became possible with the introduction of the Programmable Pacemaker.

Currently, different kinds of these pacemakers are available, which allow the adjustment of their function to different states of healthy or sick organism without causing any discomfort to the patient.

Programmable pacemakers are insensitive to the needs of the organism and their functioning is to be changed from the outside, so that their adaptability is relative. There are other kinds of pacemakers which are more physiological, that is to say, more capable of meeting the organic needs at every moment, with its continues fluctuation. In cases where the formation of the cardiac stimulus in the atria is maintained, and the problem lies on the conduction block between the atria and the ventricles, a kind of pacemaker which senses atrial activity and then stimulates the ventricles can be introduced. These are the "atrial triggered" pacemakers, which constitute a practical reality, once the problems of implanting two catheters, one in the auricle and the other in the ventricle, are solved. In these pacemakers, as the variations in the atrial rhythm depend on organic needs variations, the pacemaker is led by the body needs Currently, for cases where it is not possible to use atrial guidance, pacemakers have been developed that are capable of sensing other parameters in the body activity, changing automatically their frequency (self-programming frequency pacemakers). Some pacemakers catch vibrations of the body during movement; others detect breathing activity and accelerate frequency of the heart in combination with the frequency of breathing; others detect fine vibrations in the cardiac electric activity caused by exercise and others being at the stage of design or project respond to the exhaustion of oxygen in blood, to changes in body temperature, or even to many of these causes.

First pacemakers were big and short-lasting. They weighted one hundred grams, had a diameter of 7-8 cm, and 2-3 cm of thickness, wrapped with silicone rubber toughly applied. They were fed by mercury-zinc batteries that could last no more than 2-3 years. Electrodes broke frequently because of the phenomenon called "fatigue of materials".

Nowadays, size has been reduced by a quarter or a fifth, weight has been reduced to less than a third, duration reaches 5-10 years according to the designs, and electrodes are made of a certain design and material that practically prevent their breaking and allow energy savings.

At present, we have smaller pacemakers, more powerful, long lasting, more versatile and more comfortable for the patient.

Traditional ventricular stimulation in the apex of the right ventricle (RV) is well known in the art, which through several years of use, it has shown an important reliance as regards permanence of the catheter in the correct place, control of the cardiac frequency and facility for its implantation. FIG. 9 illustrates a chart that shows right ventricular stimulation, "Standard Bipolar Stimulation on apex of RV". However, day after day it is proven that regardless of the fact that it keeps atrio-ventricular synchrony through stimulation of both chambers, results are far away from causing a real physiological synchrony. Right ventricular stimulation on the apex of RV generates a pattern of electric activation, asynchronous in itself and therefore asynchronous left ventricular contraction.

On the other hand, stimulation in the apex of the RV can lead to non-homogenous left ventricular contraction, myofibril erradication, and disorders of myocardic perfussion. This generates an increase in the morbidity and mortality of these patients, therefore leading from several years ago to look for other places of unique and simultaneous stimulation in order to improve electric and hemodynamic parameters of permanent stimulation.

As it can be seen novelty in pacemakers was only slightly related to the place of application of electrodes. In the new pacemaker of my invention, it can be seen as an advantage, apart from those described in the previous art, when applied on patients with pacemaker indication with preserved interventricular contraction, it prevents from deleterious effects of the traditional pacemaker over the ventricular function.

Also there are some advantages for patients with disorders in intraventricular impulse conduction and allows the re-establishment of the normal intraventricular activation sequency.

Other advantage is that in patients who suffered from heart failure with blockage in its left branch, allows me to apply well-known advantages of re-synchronization through using only one catheter, so as to obtain the electric alternative circuit procedure that we herewith call EB Electric Bypass.

As already known, traditional ventricular stimulation in the apex of right ventricle (RV) has shown along the years, great trust as regards its permanence, control of the cardiac frequency and ease for its introduction. However, day by day it has been proved that regardless the fact that it keeps atrio-ventricular synchrony through stimulation of both chambers, results are far away of causing a real phyisological synchrony. Right ventricular stimulation on apex of RV generates a pattern of electric activity, asynchronic in itself and therefore contraction and asynchronic left ventricular contraction.

On the other hand, stimulation in the apex of the RV can lead to non-homogenous left ventricular contraction, myofibril erradication, and disorders of myocardic perfussion. These disorders cause an increase in the morbidity and mortality of these patients, therefore leading from several years ago to look for other places of unique and simultaneous stimulation in order to improve electric and hemodynamic parameters of constant stimulation.

In the illustrative examples attached to the present invention its significant usefulness is shown, in presence of left ventricular dysfunction with dual-chamber (AV) pacing, resynchronizing its activity with only one catheter in RV septum, without the need of special electrophysiologist training, as seen in FIG. 9. Therefore the potential outbreak in the use of the pacemaker of the invention for constant stimulation is shown.

II. SUMMARY OF THE INVENTION

According to an embodiment of the present invention, a pacemaker apparatus is disclosed for use in a heart treatment environment in which the heart includes a conduction abnormality in a ventricle. Such pacemaker apparatus includes a pacing electrode located in the heart, a pulse generator that provides pacing signals to the pacing electrode in the heart, and a signal generation circuit that generates electrical signals from heart-related feedback signals that indicate that the pacing electrode is delivering the pacing signals in a region at or near the His bundle of the heart, wherein the combination of the pulse generator and the signal generation circuit indicates that the pacing electrode is delivering the pacing signals in the region, at or near the His bundle of the heart, to electrically bypass the conduction abnormality of the heart in the ventricle.

According to another embodiment of the present invention, a pacemaker apparatus is disclosed for use in a heart treatment environment in which the heart includes a conduction abnormality, the pacemaker apparatus including a pulse generator to provide pacing signals, at least one pacing electrode to carry the pacing signals between the pulse generator and a ventricle of the heart, a catheter to deliver the pacing electrode to the heart, and a guide sheath to guide the catheter and the pacing electrode to a target pacing region at or near the His bundle of the heart, the guide sheath including at least one sheath electrode to deliver pacing signals to the heart.

According to another embodiment of the present invention, a pacemaker is disclosed which reestablishes or keeps the physiological electric conduction of the heart and a method of application.

Other aspects of the invention are described in the discussion of examples that follow.

III. BRIEF DESCRIPTION OF THE DRAWINGS

FIG. 1.

Figure 5:
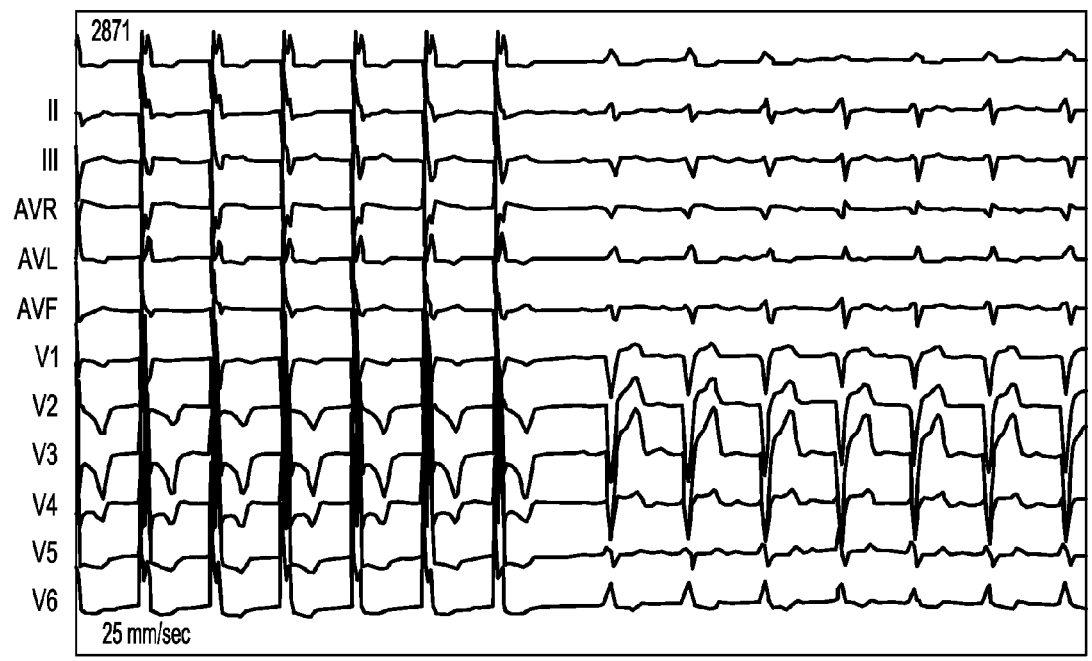

FIG. 5 shows an ECG of a patient with sinusal rhythm and complete block of the left branch, as the septal stimulation of high penetration electrical bypass stimulation according to the present invention "normalizes" the QRS, narrowing it. A proof of the "physiological change" in the sequence of intraventricular conduction is also the presence of the QRS narrowing, changes of the ventricular repolarization, with negative T waves in the precordial leads, probably secondary to "electrotonic memory".

Figure 6:
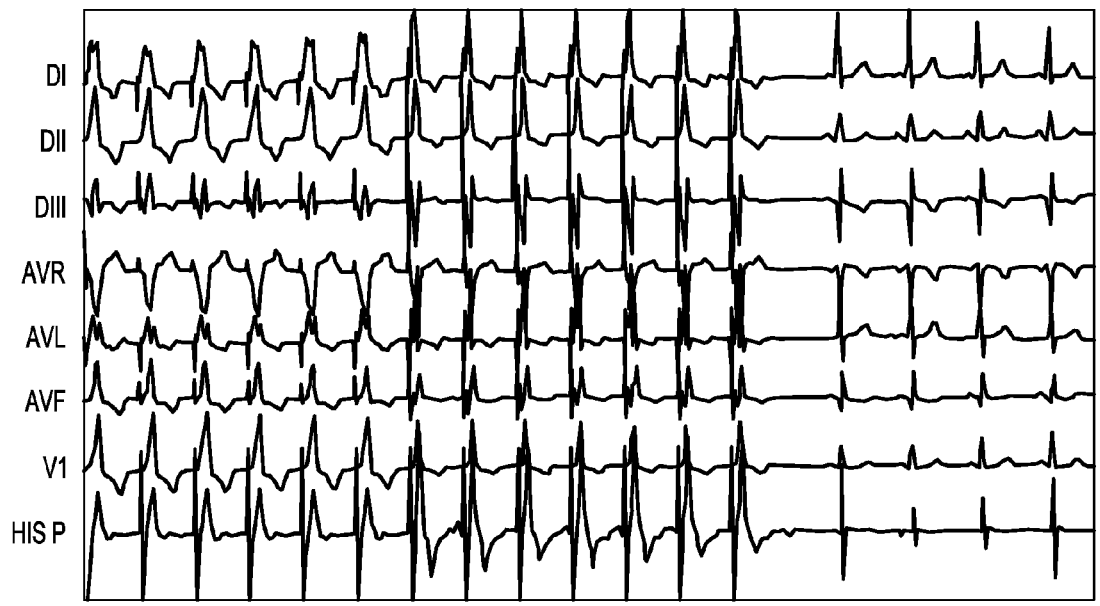

FIG. 6 is an ECG showing stimulation on apex of the right ventricle and follows a similar behavior to the presence of complete left branch block in the basal ECG and with case septal electrical bypass stimulation narrows the QRS and generates the same changes on ventricular repolarization.

Figure 7:
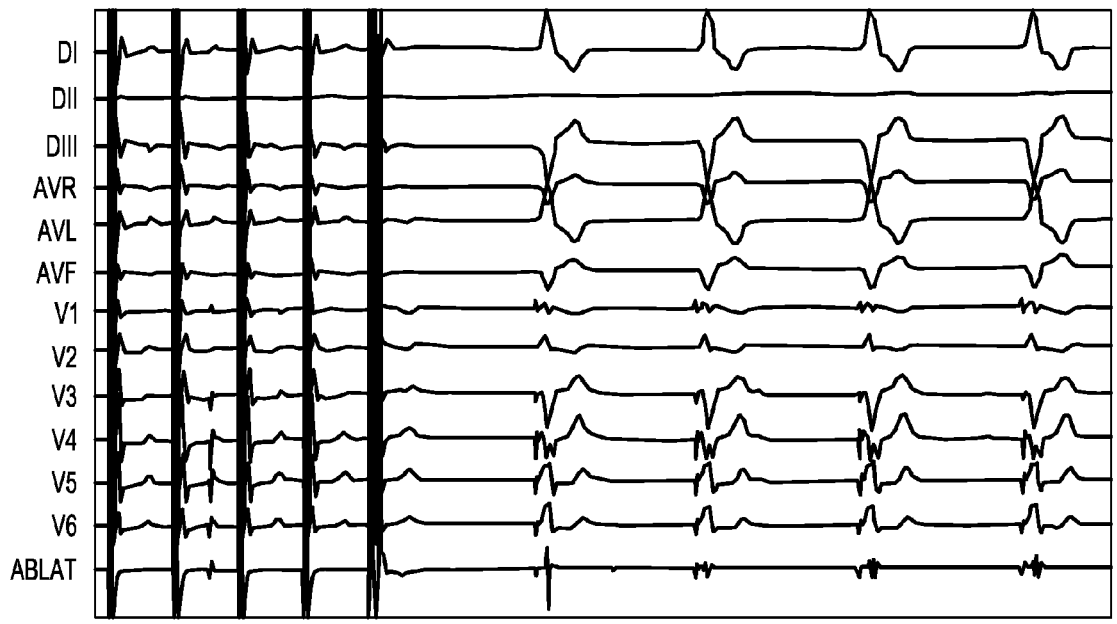

FIG. 7 is an ECG showing on its left side how EB pacing captures the ventricles with narrow QRS and normal depolarization-repolarization pattern.

Figure 8:
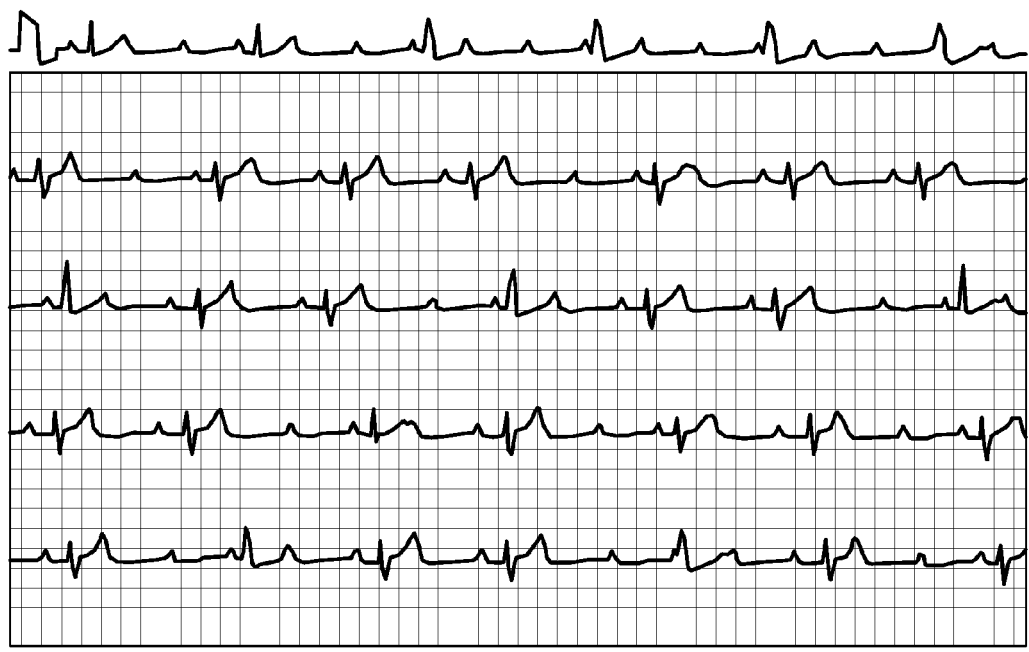

FIG. 8 is an ECG in a patient with left bundle branch block and where the fusion with extrasystoles coming from the right ventricle are expressed as a significantly narrow QRS.

Figure 9:
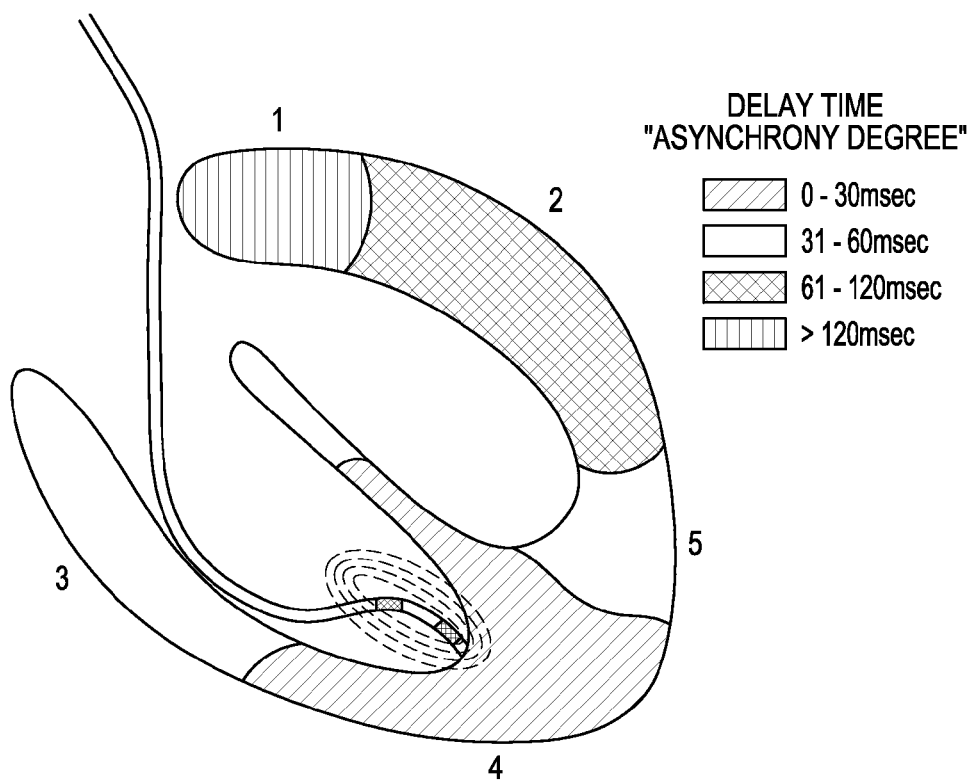

FIG. 9 is a cross section view of the heart with the electrode in Septal EB1 stimulation.

Figure 10:
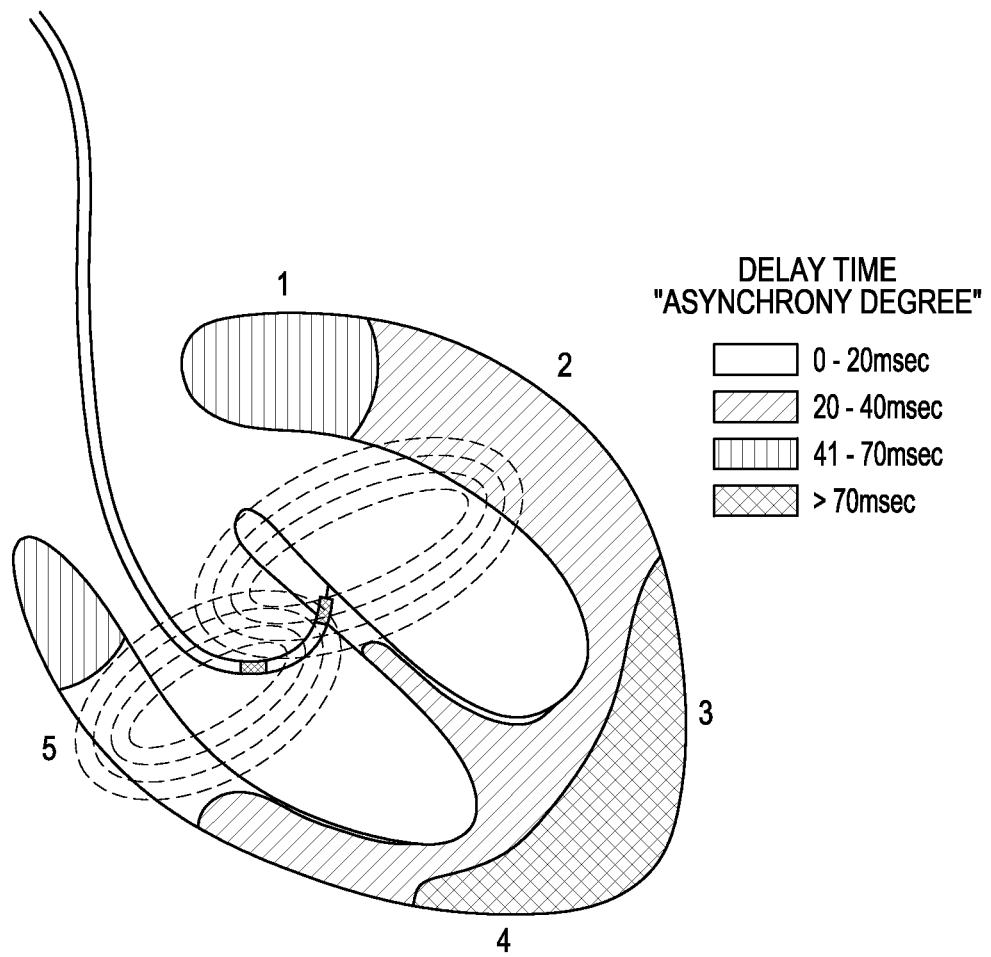

FIG. 10 is a cross section view of the heart with the electrode in septum RV stimulation.

Figure 11:
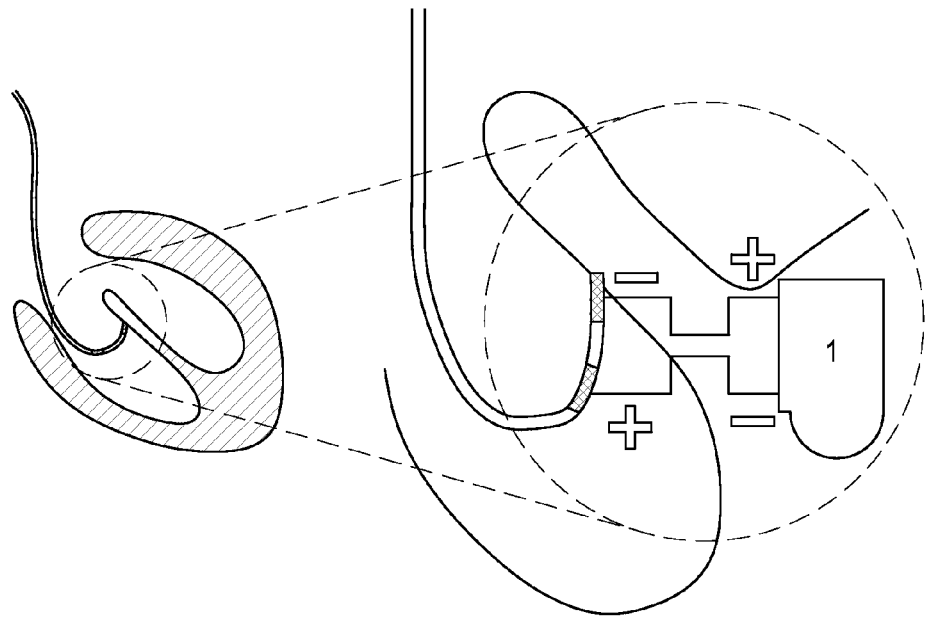

FIG. 11 is a cross section view of the heart with septal EB1 stimulation.

Figure 12:
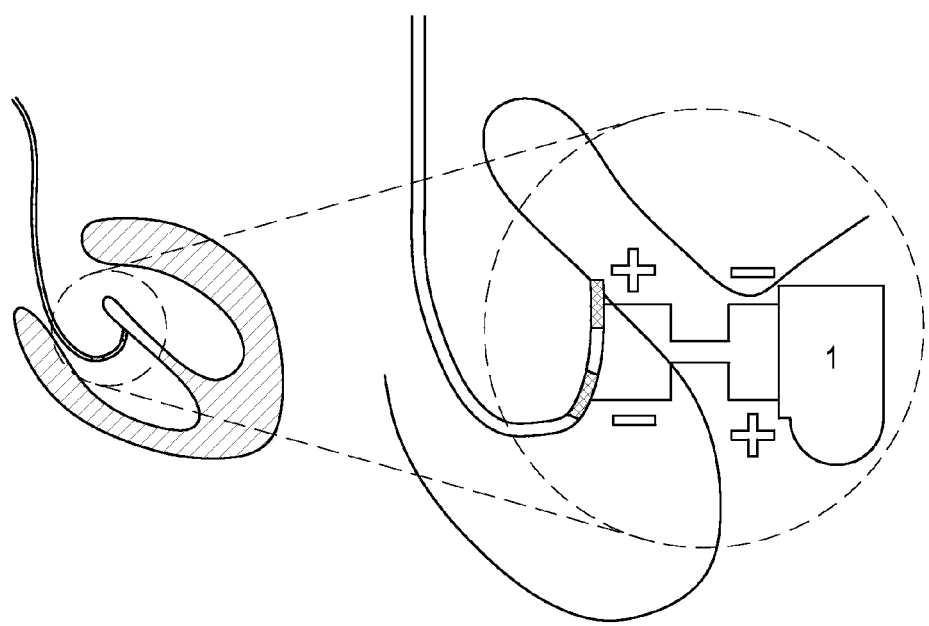

FIG. 12 is a cross section view of the heart with septal EB2 stimulation.

IV. DETAILED DESCRIPTION OF THE INVENTION

This new pacemaker is intended to render a stimulation of a high septal penetration as already mentioned called herein "EB (Electric Bypass)" as previously mentioned, and which involves a real approach to the permanent physiological pacing.

Apart from the method for application to facilitate the implantation and to avoid the connection and disconnection of the catheter, a deflectable sheath can be used with an electrode on its edge which allows a stimulation to verify the proper place and then screw the catheter in said place. This sheath is removed after finding the proper place for stimulation and is eventually disposable.

Likewise, in the present invention apart from the new pacemaker and its method of application, a new right septal stimulation is described, which allows the generation of a wave front with simultaneous ventricular depolarization and QRS narrowing either in patients with normal QRS or in those with conduction disorders.

The normal conduction throughout the His-Purkinje system produces a fast synchronic sequential depolarization of the myocardial fibers causing a more efficient ventricular contraction. It is already known that the best place for pacing to prevent the ventricular dissynchrony keeping its normal activity while applying the catheter is the His bundle.

Several methods have been developed to reach the His Bundle by septal stimulation. However there were several troubles in its implementation, requiring special treatment for finding the catheter, with variable results.

Together with the pacing system including the new pacemaker and its method of application, by septal implementation the wavefront penetration to the Hisian mainstream is obtained. The result is a narrow QRS, similar to the one in the normal conduction and with an almost normal bemodynamic efficiency.

With reference to FIGS. 11 and 12, a heart H is shown in cross-section showing a right ventricle RV and a left ventricle LV divided by a septum S. A catheter is provided in the right ventricle RV with a distal electrode 12 secured to the septum and a proximal electrode 14 in the right ventricle. The right-hand side of the figures show the catheter 10 enlarged and energized by a pacemaker 1 to create two monopolar pulsewaves between the electrodes 12, 14 and the pacemaker 1. FIGS. 11 and 12 differ only in the figures show two different phases for the pulsewaves.

The present pacemaker 1 is a pulse generator, single-chambered or dual-chambered, with conventional features: it has a ventricular output including at least two superimposed monopolar pulsewaves of reversed polarity between each other, with programmable configuration, in respect to a neutral which can be the pacemaker's metallic box or a third electrode in the case of a tripolar catheter. The distal electrode 12 of this catheter 10 is fixed in the right ventricular RV septum S for the ventricular stimulation, thus producing an electrical alternative circuit or Electrical Bypass (EB) of the bundle block, being a non-conventional cardiac stimulation application place, so we are in the presence of a new use by the creation of a virtual electrode for the physiological electric synchrony of the heart. Two charts showing two different options can be seen in FIGS. 9 and 10. One of them is entitled "Septal Stimulation EB1" and the other is entitled "Septal Stimulation EB2". In FIG. 9 (Septal Stimulation EB1), the distal electrode 14 is secured to the apex of the right ventricle RV. In FIG. 10, the distal electrode is secured to the septum S.

In each of FIGS. 9 and 10, the heart H is shown divided into regions 1-5. In FIG. 9, Region 1 is the left ventricle postero basal side. Region 2 is the left ventricle lateral. Region 3 is the right ventricle basal side. Region 4 is the apex right ventricle septum apical and Region 5 is the apex left ventricle. In FIG. 10, Region 1 is the left ventricle postero basal side. Region 2 is the left ventricle lateral. Region 3 is the apex left ventricle. Region 4 is the apex right ventricle septum apical and Region 5 is the right ventricle lateral.

In the method of application and the way to facilitate the implantation and to avoid the connection and disconnection of the catheter, a deflectable sheath with an electrode in its edge can be used, which allows stimulation, in order to check the proper place and then screw the catheter in said place. This sheath is removed after finding the proper stimulation place and is eventually disposable.

According to one example, a new pacemaker and its method of application includes the following items:

a pulse generator, single-chambered or dual-chambered, with conventional features: it has a ventricular output including at least two superimposed monopolar pulsewaves of reversed polarity between each other, with programmable configuration, in respect to a neutral which can be the pacemaker's metallic box or a third electrode in the case of a tripolar catheter;

a conventional active-fixation ventricular catheter;

a deflectable sheath with an electrode on its distal tip;

a stimulation place in the right interventricular septum;

the right interventricular septum stimulation place, is the one which allows a greater interventricular synchrony making the left stimulation easier and the application of the electric alternative circuit principle or Electrical Bypass that reestablishes the physiological conduction of the heart when damaged.

Apart from the new pacemaker and its method of application with the deflectable sheath with an electrode on its edge, the present invention describes a new technique for the right septal stimulation which allows the generation of a wave front with simultaneous ventricular depolarization and QRS narrowing either in patients with normal QRS or in those with conduction disorders.

This is obtained by the formation of a virtual electrode which generates a stimulation field significantly higher than the one in a traditional electrode for the physiological stimulation. Said higher current field allows to compromise more distant areas than the pacemaker place even overcoming conduction disorders, —electrical bypass (EB)—. The use of said virtual electrode assures an energy saving with regards to the necessary high output and makes the placing in the septum easier avoiding difficult electrophysiological mapping procedures.

For a better comprehension of the present invention, a septal ventricular stimulation system with high performance in the electric and probably contractile synchrony, is described. This system is intended to significantly modify the definitive pacemaker implantation, making it more physiological. Patients with QRS narrowing were tested, as well as patients with AV atrio-ventricular and interventricular conduction disturbances, showing in all of them the QRS narrowing phenomena and the orientation of the depolarization with vectors similar to those in the depolarization through the His-Purkinje system.

EXAMPLES

The embodiments of my invention are shown in the application of traditional pacemakers made in 50 consecutive patients who were stimulated in right septum with standard bipolar catheters. They were used for the record of the His bundle activity and with the pacing technique of my invention, pacemakers, method of application and a special high penetration technique of system EB.

In order to use a conventional voltage a pulse generator driven by a traditional over-stimulation pacemaker was used, with programming outputs from 1 to 36 volts and two types of waves, a sequential biphasic and another superimposed biphasic wave, with pulse widths programmable from 0.1 to 2 milliseconds. The second wave uses each electrode individually with reference to an indifferent one with opposed polarities. This allows the use of a traditional output and generating a virtual electrode of great magnitude of current which is the objective of EB stimulation (Electrical Bypass), and reducing the use of high energy with the results previously tested.

In order to know the behavior of the left ventricle in normal patients and with several branch conduction disturbances, a multipolar catheter through the coronary sinus was used. The distal dipole represents the side basal portions of the left ventricle, as it was recently shown by CARTO® search.

Forty-nine patients were successively analyzed at the EP Lab during the procedures to evaluate sinus function and A-V conduction.

These patients were divided in two groups:

Group A (31 patients) was tested with pacing on edge of RV and in septum with high output (20 volt).

Group B (18 patients) was tested with the pacing stimulation of my invention, with the EB alternative electric pathway in septum.

In both groups the duration of the QRS was measured, both the basal as well as during the different types of stimulation. In order to test the activation in basal and distal portions of the left ventricle, the gap between the beginning of the QRS and the depolarization in the coronary sinus of the most distant portion of the left ventricle was measured.

Table 1 describes the results in relation to features and magnitude of the width of the QRS obtained in each case.

|    | QRS           | BASAL | sSEP | sAPEX | R-VI | EB-VI | SVD-VI | EST   |
|----|---------------|-------|------|-------|------|-------|--------|-------|
| 1  | BCRI          | 160   | 100  | —     | —    | —     | —      | EB    |
| 2  | BCRI          | 220   | 140  | —     | —    | —     | —      | EB    |
| 3  | BCRI          | 215   | 154  | 214   | 154  | 90    | 169    | EB    |
| 4  | BCRI          | 140   | 90   | 120   | 80   | 70    | 90     | EB    |
| 5  | BCRI          | 180   | 128  | —     | 120  | 76    | —      | EB    |
| 6  | ANG           | 92    | 104  | 144   | —    | —     | —      | EB    |
| 7  | ANG           | 120   | 150  | 240   | —    | —     | —      | EB    |
| 8  | ANG           | 84    | 96   | 140   | 40   | 64    | 112    | EB    |
| 9  | ANG           | 80    | 88   | 120   | 36   | 42    | 86     | EB    |
| 10 | ANG           | 72    | 88   | 120   | 40   | 68    | 92     | EB    |
| 11 | ANG           | 78    | 82   | 144   | 58   | 58    | 100    | EB    |
| 12 | BCRD          | 150   | 150  | —     | —    | —     | —      | EB    |
| 13 | HBAI          | 90    | 100  | 150   | —    | —     | —      | EB    |
| 14 | BCRD + HBAI   | 146   | 120  | 165   | —    | —     | —      | EB    |
| 15 | BCRD          | 120   | 110  | 150   | —    | —     | —      | EB    |
| 16 | ANG           | 60    | 70   | —     | —    | —     | —      | EB    |
| 17 | BCRD + HBAI   | 120   | 130  | 190   | —    | —     | —      | EB    |
| 18 | BCRD + HBAI   | 140   | 100  | —     | 68   | 70    | 98     | EB    |
| 19 | ANG           | 70    | 85   | —     | —    | —     | —      | 20 mA |
| 20 | ANG           | 80    | 100  | —     | —    | —     | —      | 20 mA |
| 21 | HBAI          | 100   | 110  | 180   | —    | —     | —      | 20 mA |
| 22 | BCRD + HBAI   | 160   | 120  | 190   | —    | —     | —      | 20 mA |
| 23 | ANG           | 90    | 100  | —     | —    | —     | —      | 20 mA |
| 24 | ANG           | 70    | 85   | —     | —    | —     | —      | 20 mA |
| 25 | ANG           | 80    | 100  | 180   | —    | —     | —      | 20 mA |
| 26 | ANG           | 80    | 100  | —     | —    | —     | —      | 20 mA |
| 27 | ANG           | 70    | 100  | —     | —    | —     | —      | 20 mA |
| 28 | ANG           | 65    | 90   | —     | —    | —     | —      | 20 mA |
| 29 | BCRD          | 110   | 140  | —     | —    | —     | —      | 20 mA |
| 30 | ANG           | 60    | 70   | —     | —    | —     | —      | 20 mA |
| 31 | ANG           | 60    | 65   | —     | —    | —     | —      | 20 mA |
| 32 | ANG           | 80    | 90   | —     | —    | —     | —      | 20 mA |
| 33 | ANG           | 80    | 90   | —     | —    | —     | —      | 20 mA |
| 34 | ANG           | 50    | 80   | 110   | —    | —     | —      | 20 mA |
| 35 | ANG           | 60    | 76   | —     | —    | —     | —      | 20 mA |
| 36 | HBAI          | 100   | 170  | —     | —    | —     | —      | 20 mA |
| 37 | BCRD + HABI   | 120   | 125  | 170   | —    | —     | —      | 20 mA |

-continued

| | QRS | BASAL | sSEP | sAPEX | R-VI | EB-VI | SVD-VI | EST |
|---|---|---|---|---|---|---|---|---|
| 38 | HBAI | 80 | 100 | 170 | — | — | — | 20 mA |
| 39 | HBAI | 50 | 100 | 160 | — | — | — | 20 mA |
| 40 | BCRD | 64 | 70 | — | — | — | — | 20 mA |
| 41 | ANG | 55 | 130 | 160 | — | — | — | 20 mA |
| 42 | ANG | 60 | 70 | — | — | — | — | 20 mA |
| 43 | ANG | 90 | 100 | 140 | — | — | — | 20 mA |
| 44 | BCRI | 100 | 120 | 180 | — | — | — | 20 mA |
| 45 | ANG | 70 | 110 | — | — | — | — | 20 mA |
| 46 | ANG | 80 | 95 | — | — | — | — | 20 mA |
| 47 | BCRD + HABI | 120 | 130 | 180 | — | — | — | 20 mA |
| 48 | ANG | 85 | 140 | — | — | — | — | 20 mA |
| 49 | ANG | 70 | 85 | — | — | — | — | 20 mA |
| 50 | ANG | 120 | 140 | 180 | — | — | — | 20 mA |

References:
measures are expressed in milliseconds;
narrow ANG = QRS lower than 100 msec;
sSEP = width of QRS in septal stimulation;
sAPEX = width of QRS with stimulation from apex of RV;
R-LF = conduction time from R to a record of RV from the coronary cavity;
EB-RV = conduction time from septal stimulation EB to a record of RV from the coronary cavity;
sRV-LV = conduction time from stimulation on apex of RV to a record of the LV from coronary cavity;
EST = features of stimulation; 20 mA = traditional stimulation with output of 20 mAmperes.

As described in the table above, there are no major differences between QRS EB and the spontaneous QRS. The average, QRS EB has 14 msec more than the spontaneous QRS. This delay is caused by a delta wave at the beginning of the QRS due to the septal penetration through a muscular pathway before the arrival of the stimulus to the specialized conduction system. Then the remaining depolarization is exactly the same as the normal QRS configuration. Differences regarding septal stimulation were not observed either when it was performed with higher energy (20 volts).

In the cases where RV apex was paced, a marked difference in spike-to-LV interval versus spike-to-LV (EB) interval was observed, LV activity being recorded as previously explained from the distal dipole of a multipolar catheter located in the coronary sinus. In average, the conduction time from the apex of RV to LV is increased by 54 msec in respect to the septal stimulation time EB to LV. This significant shortage of left-ventricle to right-ventricle time is also registered because of the presence of complete left branch block in the basal ECG, wherein the QRS significantly narrows (39 msec average) after EB stimulation. It is also accompanied by significant narrowing of the QRS in both cases (61 msec average), which supposes a more effective electric re-synchronization of the left ventricle.

Figure 1:
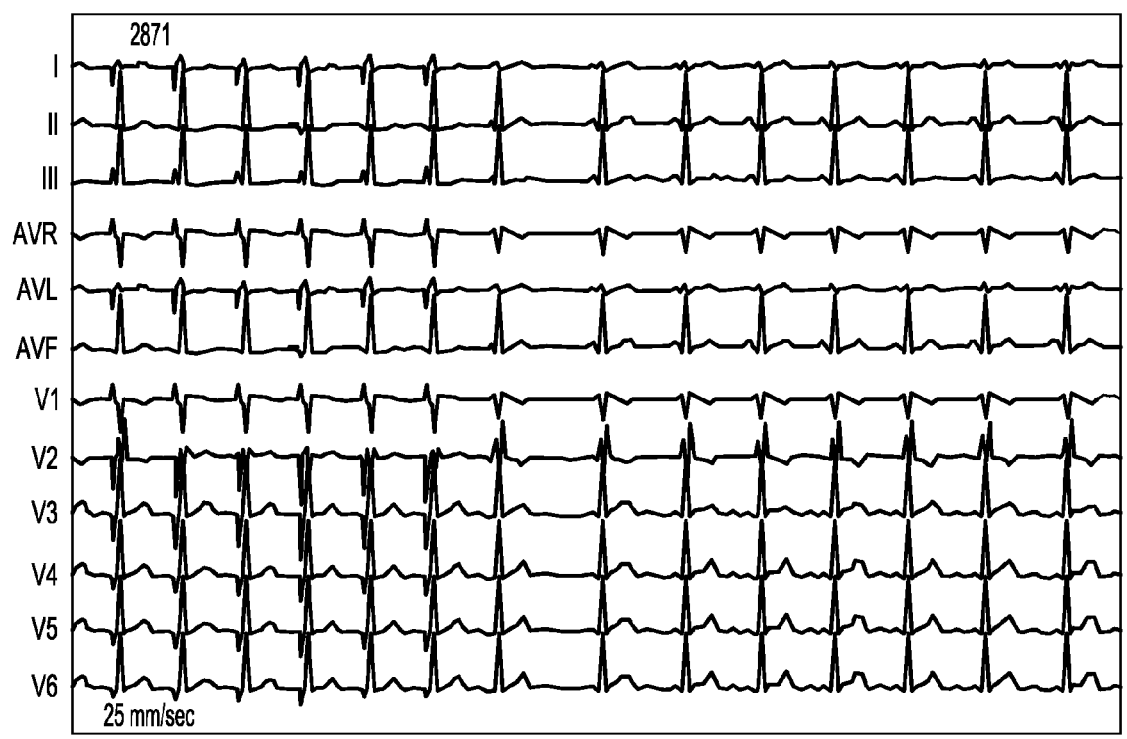
FIG. 1 shows as an example of first case patient with an electrophysiology recording showing a narrow QRS and a septal electrical bypass stimulation according to the present invention showing just a slight widening of the QRS (first half of the figure) with a conduction sequence similar to the one of the basal QRS.
Figure 2:
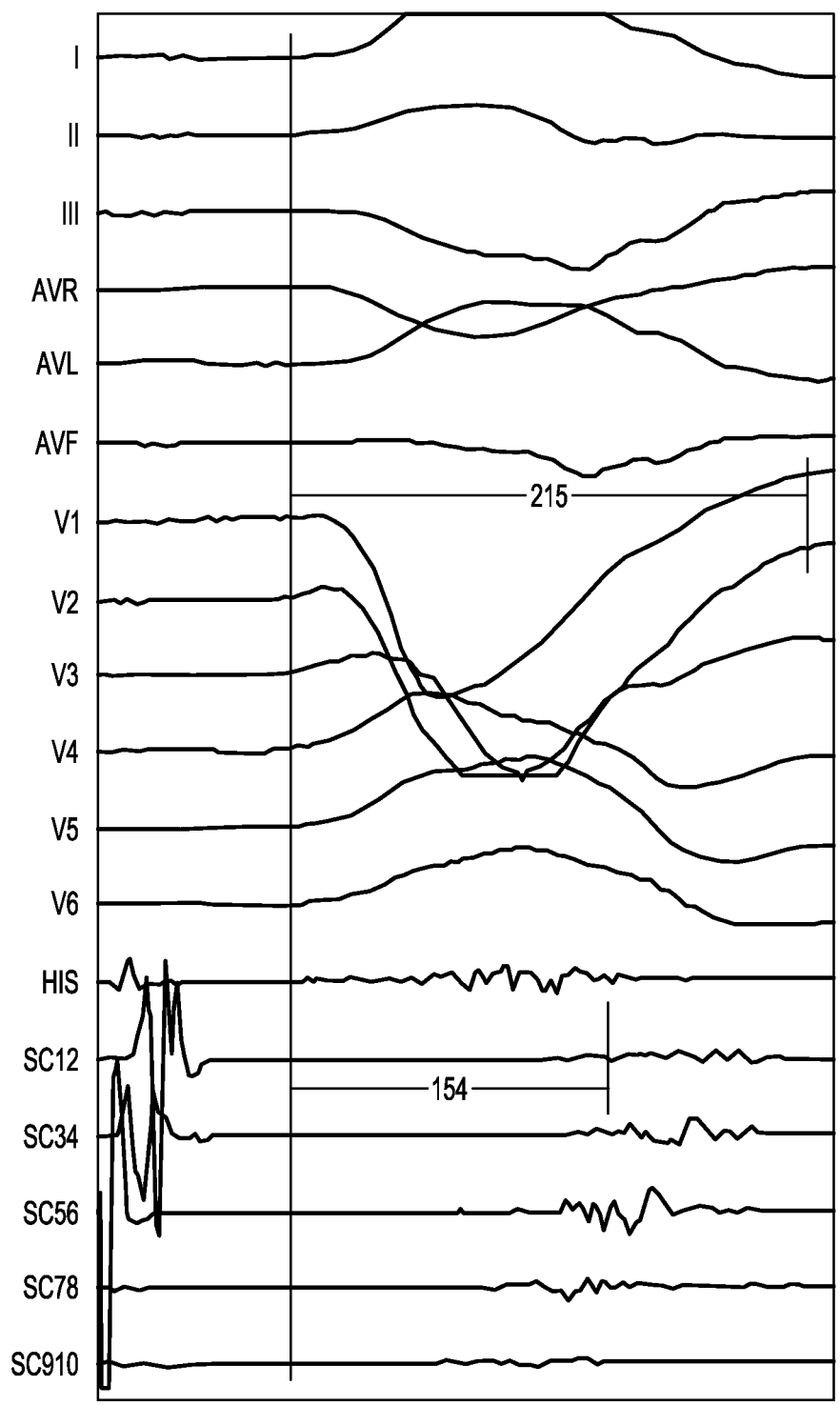
FIG. 2 is an electrophysiology recording of to a patient with a complete left branch block and ventricular malfunction, the time of basal conduction from the beginning of the QRS to the deflection corresponding to the left ventricle through the distal electrode of a multipolar catheter placed in the coronary sinus (164 msec).
Figure 3:
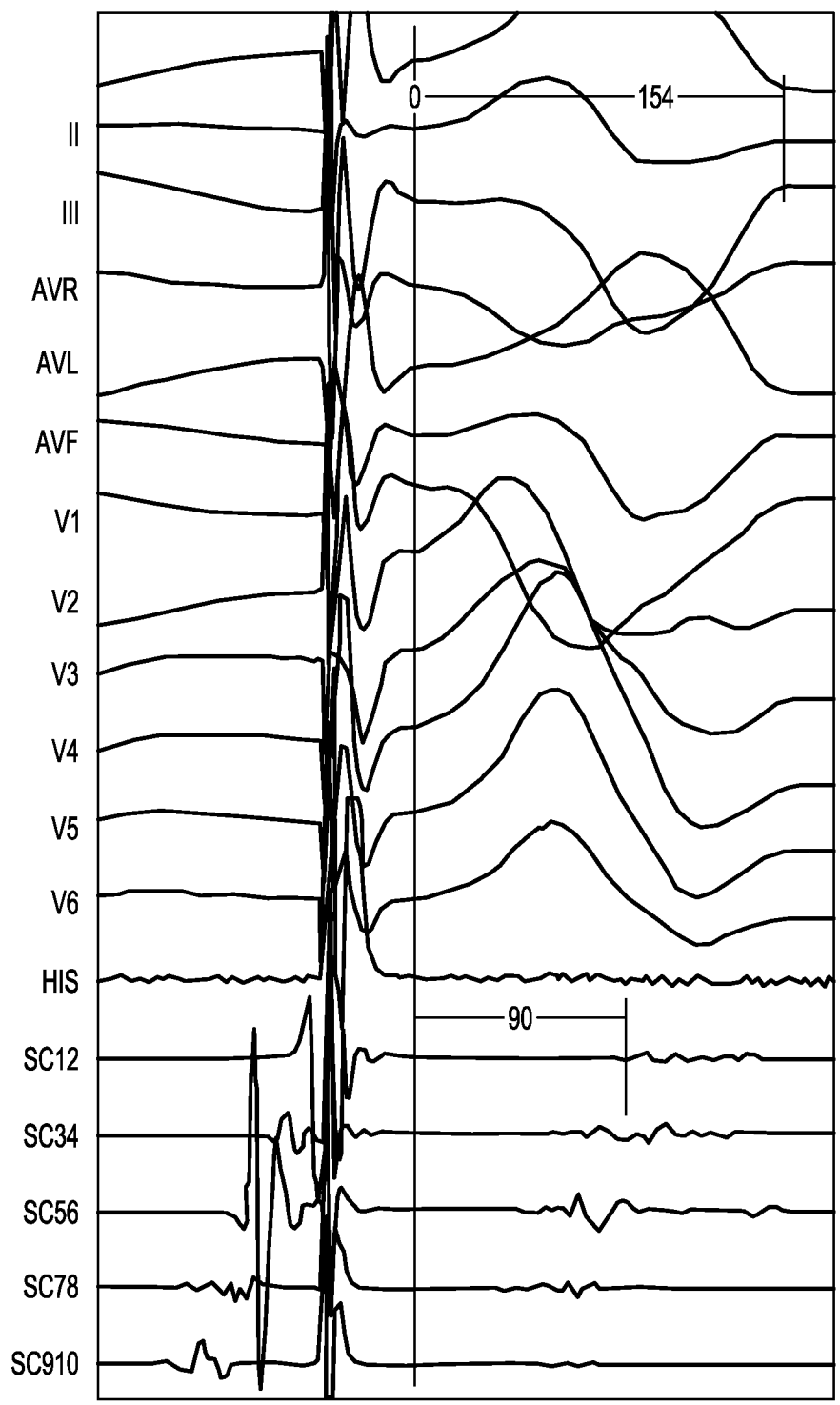
FIG. 3 is an electrophysiology recording showing the reduction of such time of conduction for the patient of FIG. 2 when electrical bypass stimulation according to the present invention is stimulated in septum (90 msec).

FIG. 1 shows as an example of case 1, a patient with narrow QRS. Septal EB stimulation shows just a slight widening of the QRS (first half of the figure) with a conduction sequence similar to the one of the basal QRS. FIG. 1. FIG. 2 corresponds to a patient with a complete left branch block and ventricular malfunction, the time of basal conduction from the beginning of the QRS to the deflection corresponding to the left ventricle through the distal electrode of a multipolar catheter placed in the coronary sinus (164 msec). FIG. 3 shows the reduction of such time of conduction when EB is stimulated in septum (90 msec). FIG. 3.

Figure 4:
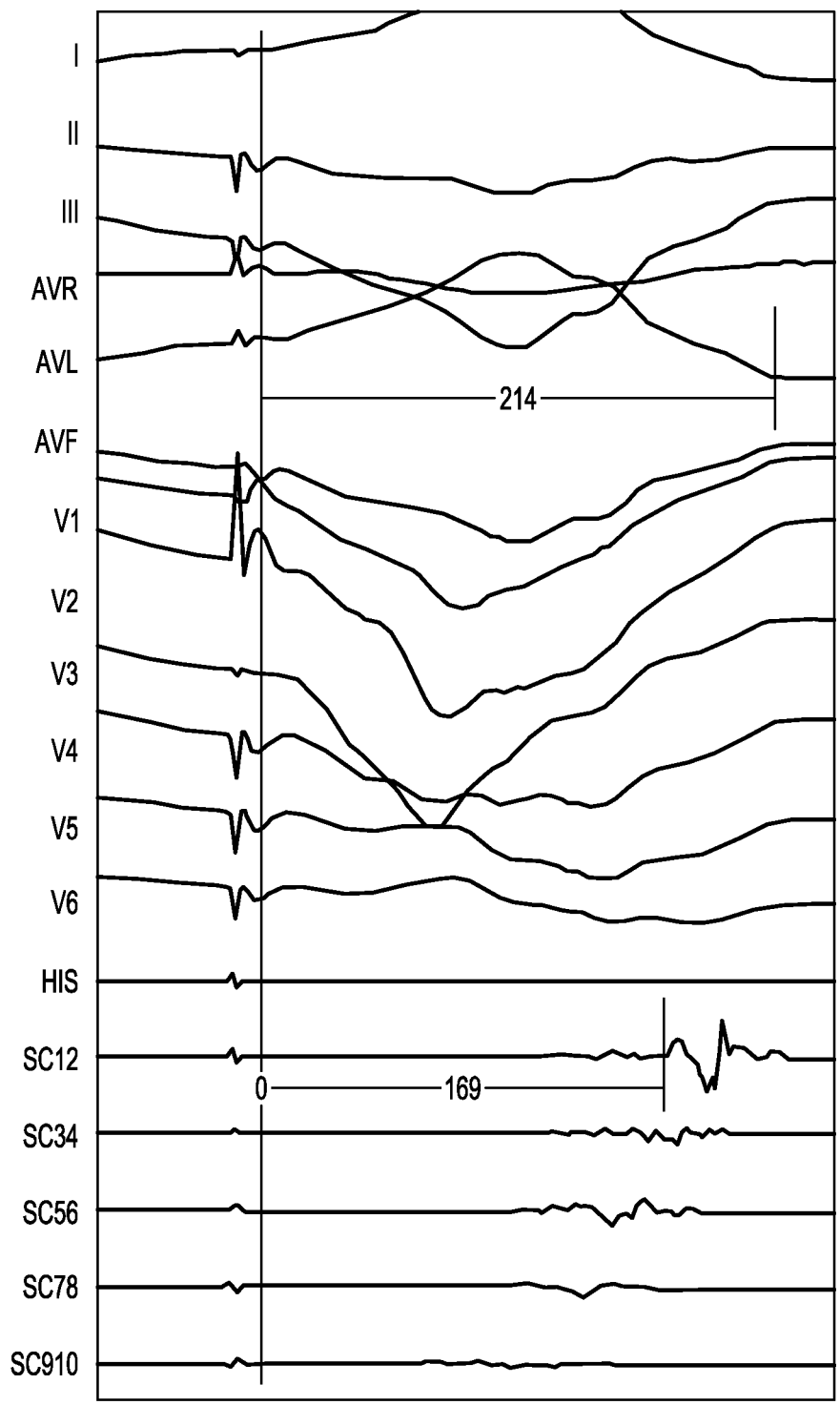
FIG. 4 is an electrophysiology recording for the patient of FIG. 2 where the electrical bypass stimulation according to the present invention is in apex of the right ventricle and keeps a conduction time to the left ventricle (169 msec) (similar to the basal time), when keeping the complete left branch block.

FIG. 4 shows the same patient, the stimulation in apex of the right ventricle keeps a conduction time to the left ventricle (169 msec (similar to the basal time), when keeping the complete left branch block. FIG. 5 shows a ECG of a patient with sinusal rhythm and complete block of the left branch, as the septal stimulation of high penetration (EB) "normalizes" the QRS, narrowing it. A proof of the "physiological" change in the sequence of intraventricular conduction is also the presence of the QRS narrowing, changes of the ventricular repolarization, with negative T waves in the precordial leads, certainly secondary to "electrotonic memory". Stimulation on apex of the right ventricle follows a behavior similar to the presence of the complete left branch block in the basal ECG. In this case septal EB stimulation narrows the QRS and generates the same changes of the ventricular repolarization (FIG. 6).

In three cases, stimulation was conducted after the radiofrequency AV node ablation, in order to avoid the high frequency response in cases of paroxystic atrial fibrillation. In these patients septal stimulation showed ventricular capture, from the same place wherein ablation was realized, with narrow QRS despite of the proper complete AV block obtained.

FIG. 7 shows the bypass of the ablation site and the narrow capture of the QRS. On the right of the record the basal rhythm is VVI pacemaker mode with complete AV block post ablation of the AV node. Note the presence of the atria dissociated from the ventricles in the "ablat" channel. At the left side, stimulation EB, from the ablation catheter in the same place of the ablation captures the ventricles with narrow QRS and normal depolarization-repolarization.

Septal EB stimulation shows a significant narrowing of the QRS similar to the normal conduction, through the His Purkinje system. It is possible to interpret this fact as an entrance of the wavefront to the His bundle, due to the special features of the EB stimulation. In some cases, the QRS similarity so suggests. However, in some circumstances, particularly when the previous QRS has a delay by the presence of the branch block, a significant narrowing is observed, similar to the one observed in the simultaneous stimulation of both ventricles (re-synchronization).

FIG. 8. In a patient with left bundle branch block, the fusion with extrasystoles coming from the right ventricle are expressed as a significantly narrow QRS.

The various embodiments described above are provided by way of illustration only and should not be construed to limit the invention. Based on the above discussion and illustrations, those skilled in the art will readily recognize that various modifications and changes may be made without strictly following the exemplary embodiments and applications illustrated and described herein. Such modifications and changes do not depart from the true spirit and scope of the present invention.

What is claimed is:

1. An apparatus comprising:
a pulse generator configured to provide electrostimulation pulses to a first electrode and a second electrode at or near a His bundle of a heart, the electrostimulation pulses comprising at least partially concurrent opposite polarity signals, wherein the electrostimulation pulses comprise a first monopolar pulse delivered from the first electrode with respect to a reference and a second monopolar pulse delivered from the second electrode with respect to the reference and
a cardiac activity monitoring circuit configured to monitor heart-related feedback indicative that a conduction abnormality of the heart is electrically bypassed during a heart contraction elicited by the electrostimulation pulses.

2. The apparatus of claim 1, further including a medium retaining data that indicates the electrode is delivering the electrostimulation pulses in the region, at or near the His bundle of the heart, to elicit the heart contraction that electrically bypasses the conduction abnormality of the heart.

3. The apparatus of claim 1, wherein the cardiac activity monitoring circuit includes an electrocardiograph (ECG) apparatus.

4. The apparatus of claim 1, wherein the cardiac activity monitoring circuit includes a sensor for indicating a delay between a beginning of a QRS complex and an activation of the left ventricle free wall at a point distal from the Apex of the left ventricle.

5. The apparatus of claim 3, wherein the ECG apparatus is configured to display a QRS width using information provided by the cardiac monitoring circuit to indicate that the pacing electrode is delivering the pacing signals in the region, at or near the His bundle of the heart, to elicit the heart contraction that electrically bypasses the conduction abnormality of the heart.

6. The apparatus of claim 3, wherein the ECG apparatus is configured to display depolarization-repolarization patterns monitored by the cardiac monitoring circuit to indicate that the pacing electrode is delivering the pacing signals in the region, at or near the His bundle of the heart, to elicit the heart contraction that electrically bypasses the conduction abnormality of the heart.

7. The apparatus of claim 1, further comprising a sensing electrode to carry the heart-related feedback signals.

8. The apparatus of claim 7, wherein the sensing electrode is one of the first or second electrodes.

9. The apparatus of claim 7, wherein the sensing electrode includes an electrode separate from the first or second electrodes and is located in the coronary sinus.

10. The apparatus of claim 1, further including a catheter to deliver the first and second electrodes to the heart ventricle.

11. The apparatus of claim 1, further including a guide sheath to guide the first and second electrodes to the region at or near the His bundle of the heart.

12. The apparatus of claim 11, wherein the guide sheath is deflectable to guide the first and second electrodes to the region at or near the His bundle of the heart.

13. The apparatus of claim 1, wherein the conduction abnormality includes a bundle branch block.

14. The apparatus of claim 1, wherein the conduction abnormality includes a ventricular conduction abnormality.

15. The apparatus of claim 1, wherein the cardiac monitoring circuit includes a cardiac electrogram monitoring circuit included as a portion of an implantable device.

16. A method comprising:
generating electrostimulation pulses for delivery to a location at or near a His bundle of a heart, the electrostimulation pulses comprising at least partially concurrent opposite polarity signals, wherein the electrostimulation pulses comprise a first monopolar pulse delivered from a first electrode with respect to a reference and a second monopolar pulse delivered from a second electrode with respect to the reference
monitoring heart signals to determine that a conduction abnormality of the heart is electrically bypassed during a heart contracting elicited in response to the electrostimulation pulses.

17. The method of claim 16, wherein monitoring heart signals to determine that a conduction abnormality of the heart is electrically bypassed in response to the electrostimulation pulses comprises using an ECG apparatus.

18. The method of claim 16, wherein monitoring heart signals to determine that a conduction abnormality of the heart is electrically bypassed in response to the electrostimulation pulses comprises using an Egram.

19. The method of claim 16, wherein monitoring heart signals includes measuring a delay between a beginning of a QRS complex and an activation of the left ventricle free wall at a point distal from the Apex of the left ventricle.

20. The method of claim 16, wherein monitoring heart signals includes monitoring a QRS width and displaying it on an electrocardiograph display to indicate that a pacing electrode is delivering the electrostimulation pulses in the region, at or near the His bundle of the heart, to elicit the heart contraction that electrically bypasses the conduction abnormality of the heart.

21. The method of claim 16, wherein monitoring heart signals includes monitoring depolarization-repolarization patterns and displaying the depolarization-repolarization patterns on an electrocardiograph display to indicate that the pacing electrode is delivering the pacing signals in the region, at or near the His bundle of the heart, to elicit the heart contraction that electrically bypasses the conduction abnormality of the heart.

22. The method of claim 16, wherein the heart signals are monitored by a sensing electrode.

23. The method of claim 22, wherein the sensing electrode is one of the first and second electrodes.

24. The method of claim 22, wherein the sensing electrode is located in the coronary sinus and is not one of the first and second electrodes.

25. The method of claim 16, further comprising using a catheter to deliver the first and second electrodes to a heart ventricle to deliver the electrostimulation pulses.

26. The method of claim 16, further comprising using a guide sheath to guide the first and second electrodes to a region at or near the His bundle of the heart.

27. The apparatus of claim 26, wherein the guide sheath is deflectable to guide the first and second electrode to the region at or near the His bundle of the heart.

* * * * *